United States Patent [19]

Nishigaki et al.

[11] Patent Number: 4,994,062
[45] Date of Patent: Feb. 19, 1991

[54] RESECTOSCOPE APPARATUS

[75] Inventors: Shinichi Nishigaki, Tokyo; Shiro Bito, Hachioji, both of Japan

[73] Assignee: Olympus Optical Co., Ltd., Tokyo, Japan

[21] Appl. No.: 355,270

[22] Filed: May 22, 1989

[30] Foreign Application Priority Data

Sep. 16, 1988 [JP] Japan .................. 63-231869

[51] Int. Cl.⁵ ........................................ A61B 17/36
[52] U.S. Cl. ................................................ 606/46
[58] Field of Search .............. 606/39, 40, 45–47; 128/4–7

[56] References Cited

U.S. PATENT DOCUMENTS

| | | | |
|---|---|---|---|
| 3,939,839 | 2/1976 | Curtiss | 606/46 |
| 3,990,456 | 4/1975 | Iglesias | |
| 4,068,667 | 1/1978 | Iglesias | 606/46 |
| 4,149,538 | 4/1979 | Mrava et al. | 606/46 |
| 4,430,996 | 2/1984 | Bonnet | 606/46 |
| 4,538,610 | 9/1985 | Kubota | 606/46 |
| 4,648,399 | 3/1987 | Nakada | 606/46 |
| 4,726,370 | 2/1988 | Karasawa et al. | 606/46 X |
| 4,744,361 | 5/1988 | Karasawa | 606/46 |

FOREIGN PATENT DOCUMENTS 60-149616 10/1985 Japan .

*Primary Examiner*—Robert A. Hafer
*Assistant Examiner*—Kerry Owens

[57] ABSTRACT

The resectoscope apparatus of this invention comprises an elongate hollow sheath to be inserted into a body cavity, an electrode inserted through the sheath and resecting or coagulating tissues within the body cavity by using a high frequency current, an endoscope insertable part inserted through the sheath and having an optical system making the body cavity interior observable and an operating part having a guide tube part through which the endoscope insertable part is inserted and a sheath connecting part connected to the base end part of the sheath and making the electrode operable from outside the body. At least one of the guide tube part and sheath connecting part is formed of an electric insulating material for electric insulation.

8 Claims, 23 Drawing Sheets

FIG.17
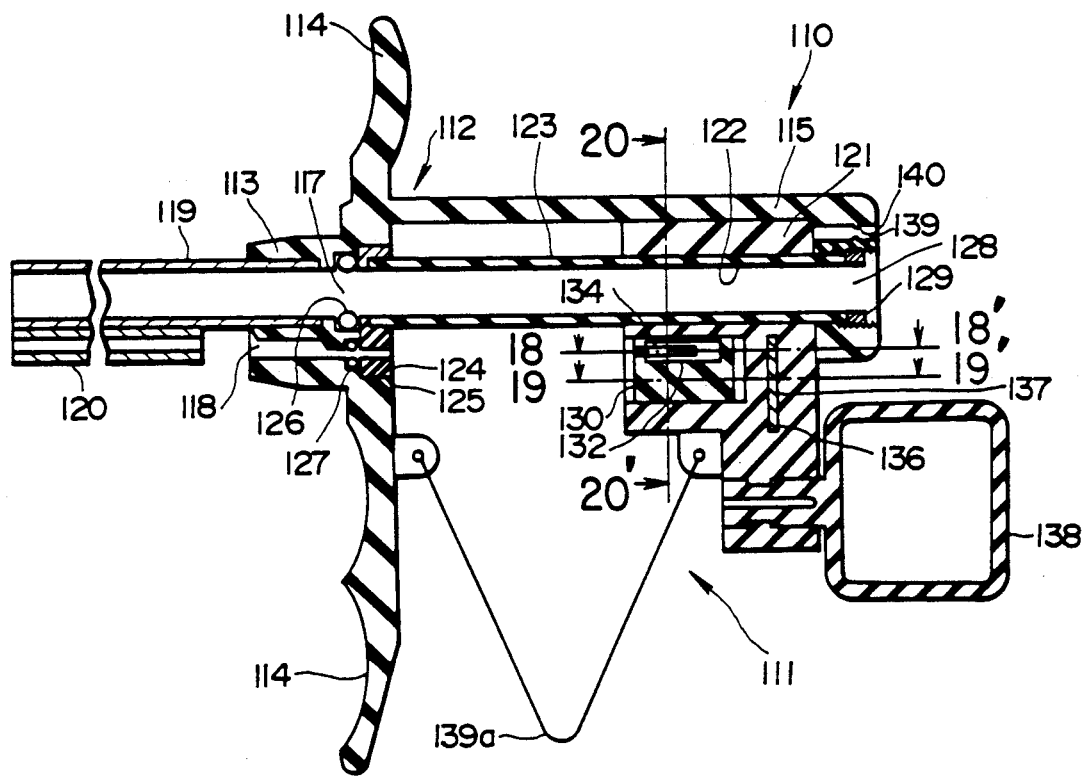
FIG.18  FIG.19  FIG.20
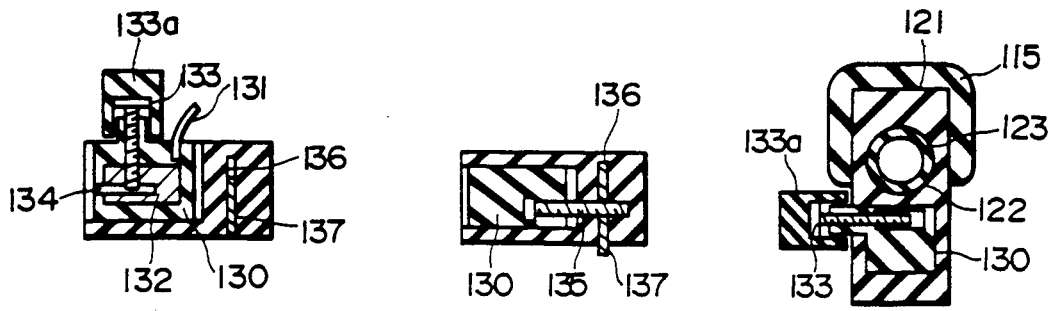

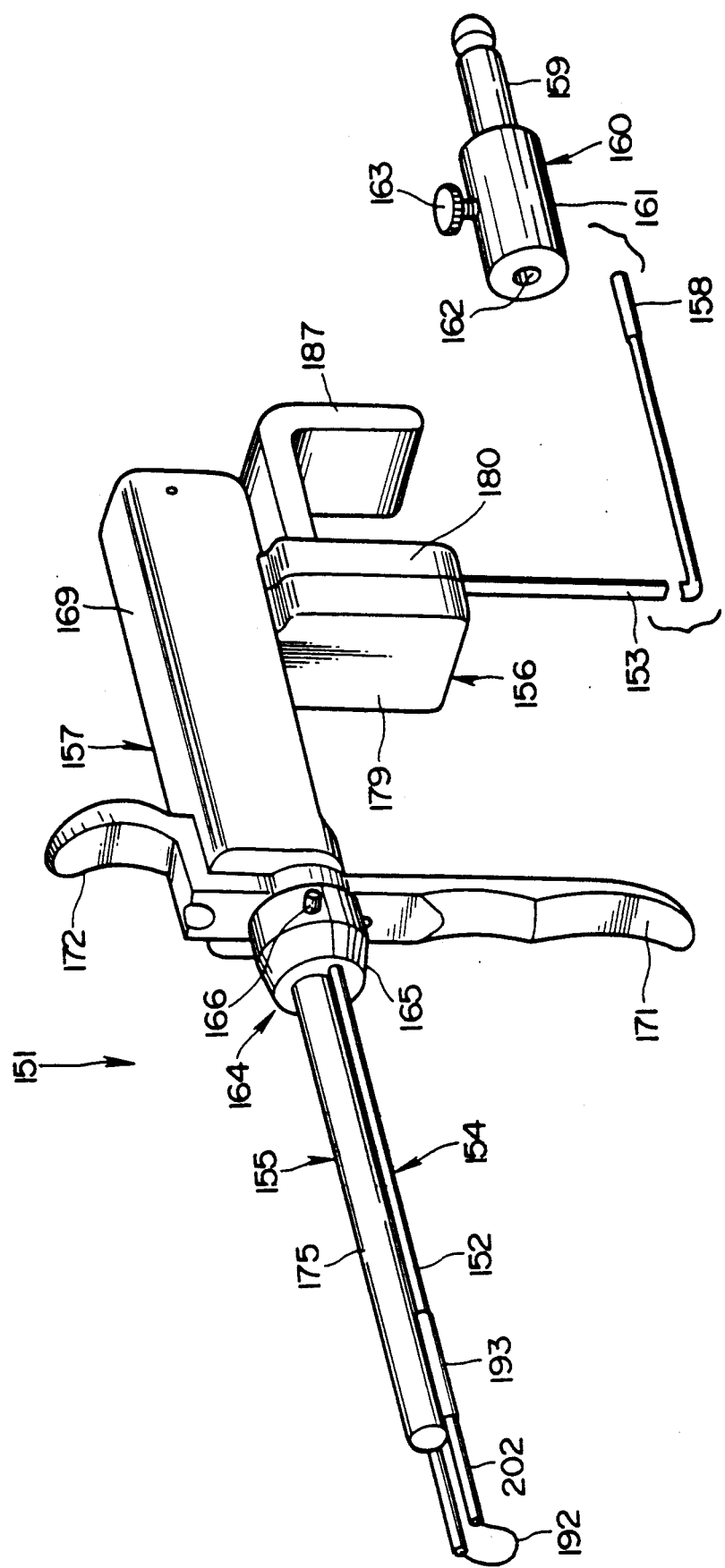

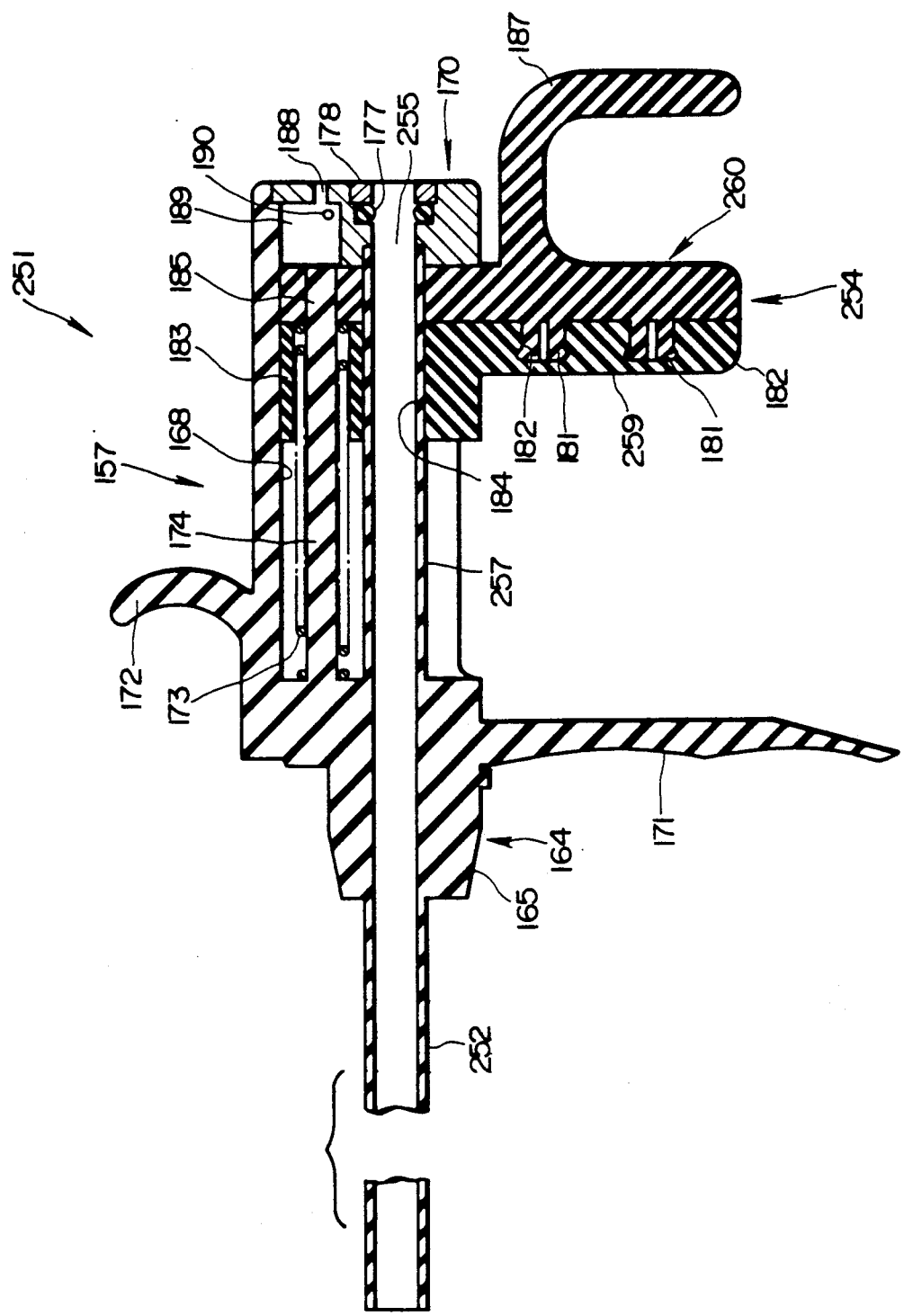

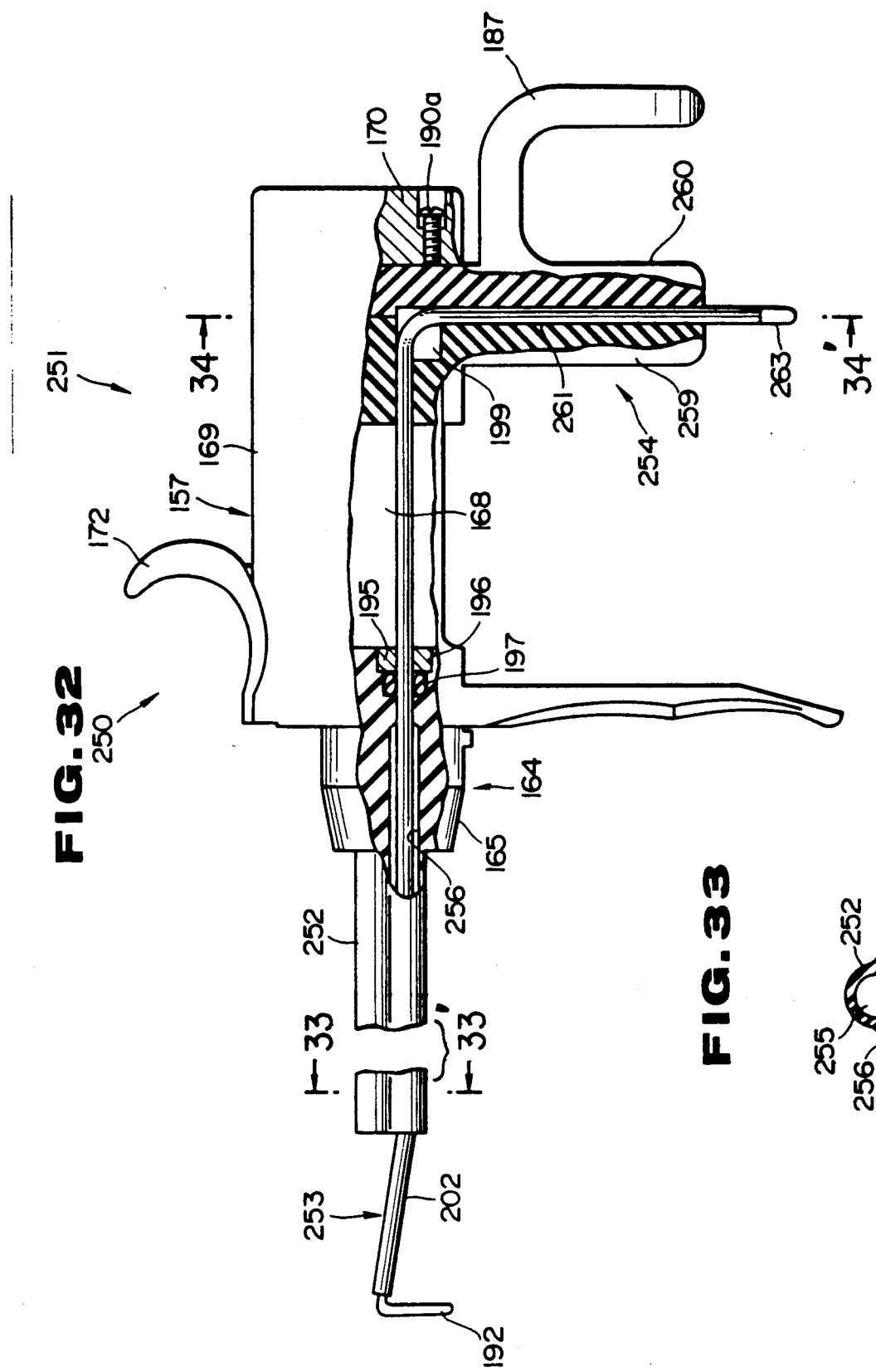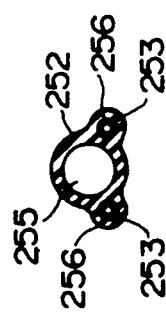

RESECTOSCOPE APPARATUS

FIELD AND BACKGROUND OF THE INVENTION

This invention relates to a resectoscope apparatus for resecting and coagulating tissues within a body cavity.

Recently, there is extensively utilized an endoscope apparatus whereby internal organs within a body cavity can be observed by inserting an elongate insertable part into the body cavity or various therapeutic treatments can be made, as required, by using treating instruments inserted through a treating instrument channel.

As the above mentioned endoscope apparatus, there is a high frequency endoscope apparatus for resecting a prostate, uterus interior, ureter interior or renal pelvis interior. As such high frequency endoscope apparatus, there is a resectoscope apparatus whereby such treatment as the resection of a prostate can be made by inserting the insertable part into the bladder through the urethra and passing a high frequency electric current through a resecting electrode as shown, for example, in the publication of a Japanese Utility Model Application No. 149616/1985.

Generally, a resectoscope apparatus comprises a hollow sheath to be inserted into a body cavity, an operating part having a slider removably fitted to the rear end side of this sheath and an observing scope (optical sighting tube) removably fitted from, the rear end side of this operating part which can project out of and retract into the rear end side of the operating part and an electrode made like a loop and branched into two branches at the tip for the resection of tissues within a body cavity. The operating part is provided with a guide tube made of a metal to insert the scope. The guide tube projects forward from a metal sheath connecting part of the operating part where it is inserted into the sheath and is provided on the outer periphery rearward from the sheath connecting part with the above mentioned slider so as to be slidable forward and rearward. An electrode inserting tube inserting and guiding the above mentioned electrode is provided in parallel with the guide tube. The electrode inserted through this electrode inserting tube is inserted further into an electrode inserting hole of the above mentioned slider and is fixed to an electric contact within the slider. When the electrode is contacted with an affected part and the slider is moved forward and rearward while flowing a high frequency electric current, with the forward and rearward movements of the electrode, the affected part will be able to be resected or coagulated.

However, in the resectoscope apparatus of such formation as is mentioned above, such liquid as an irrigating liquid is likely to enter the electrode inserting hole and, in case the liquid comes in, an electric path will be formed between the guide tube and electric contact and the electric current will leak into the guide tube.

In case the slider is moved forward, the slider will be in close contact with the sheath connecting part and therefore the current will leak between the electrode contact and sheath connecting part.

If the current thus leaks between the electric contact and guide tube or sheath connecting part, it will flow from the sheath or operating part to the patient and operator and will be likely to cause a burn or electric shock.

OBJECT AND SUMMARY OF THE INVENTION

An object of the invention is to provide a resectoscope apparatus which prevents a leaking electric current from flowing to the patient and operator through a sheath connecting part and guide tube, has no such danger as a burn or electric shock and is high in the electric safety.

In the resectoscope apparatus of the present invention, a sheath connecting part connecting an operating part and sheath with each other or a guide tube is formed of an electric insulating material at least in a part so that no electric path may be formed.

BRIEF DESCRIPTION OF THE DRAWINGS

FIG. 1 is an explanatorY view of the entire formation of a resectoscope apparatus.

FIG. 2 is an explanatory view of an electric contact and guide tube as short-circuited with each other.

FIG. 3 is a sectioned view in the direction A—A' in FIG. 1.

FIG. 5 is a perspective view of the whole of an operating part formed of plastics.

FIG. 6 is a sectioned view of an operating part.

FIG. 7 is a sectioned view in the direction B—B' in FIG. 6.

FIG. 8 is a sectioned view in the direction C—C' in FIG. 6.

FIG. 9 is a sectioned view in the direction D—D' in FIG. 8.

FIG. 10 is a disassembled view of main members in the rear of the operating part.

FIG. 11 is a sectioned view in the direction E—E' in FIG. 6.

FIG. 12 a perspective view of an optical sighting tube.

FIG. 13 is an explanatory view of the formation of an electrode receptacle and is a sectioned view in the direction C—C' in FIG. 6.

FIG. 14 is a sectioned view in the direction F—F' in FIG. 13.

FIG. 15 to 20 relate to the fifth embodiment of the present invention.

FIG. 15 is an entire appearance view of an operating part having a guide tube made of a metal and a guide tube made of an electric insulating material.

FIG. 16 is an explanatory view of the rear of an operating part.

FIG. 17 is a sectioned view of an operating part.

FIG. 18 is a sectioned view in the direction G—G' in FIG. 17.

FIG. 19 is a sectioned view in the direction H—H' in FIG. 17.

FIG. 20 is a sectioned view in the direction I—I' in FIG. 17.

FIGS. 21 to 28 relate to the sixth embodiment of the present invention.

FIG. 21 is an explanatory view of the entire formation of an operating part having a guide tube formed of an electric insulating material.

FIG. 22 is a sectioned view of an operating part.

FIG. 23 is a sectioned view in the direction J—J' in FIG. 22.

FIG. 24 is a sectioned view in the direction K—K' in FIG. 22.

FIG. 25 is an explanatory view of an electrode provided within an operating part.

FIG. 26 is a sectioned view in the direction L—L' in FIG. 25.

FIG. 27 is an explanatory view of an electrode.

FIG. 28 is an explanatory view of an electrode provided within a sheath.

FIGS. 30 to 35 relate to the eighth embodiment of the present invention.

FIG. 30 is an explanatory view of the whole of an operating part having a guide tube and body integrally molded.

FIG. 31 is a sectioned view of an operating part.

FIG. 32 is an explanatory view of an electrode within an operating part.

FIG. 33 is a sectioned view in the direction M—M' in FIG. 33.

FIG. 34 is a sectioned view in the direction N—N' in FIG. 32.

FIG. 35 is an explanatory view of an electrode.

FIG. 36 is an explanatory view of the whole of an operating part of a cylindrical cross-section.

FIG. 37 is a sectioned view of an operating part.

FIG. 38 is a sectioned view in the direction O—O' in FIG. 37.

FIG. 39 is a sectioned view in the direction P—P' in FIG. 37.

FIG. 40 is an explanatory view of an electrode.

DETAILED DESCRIPTION OF PREFERRED EMBODIMENTS OF THE INVENTION

Embodiments of the present invention shall be concretely described in the following with reference to the drawings.

Figure 1:
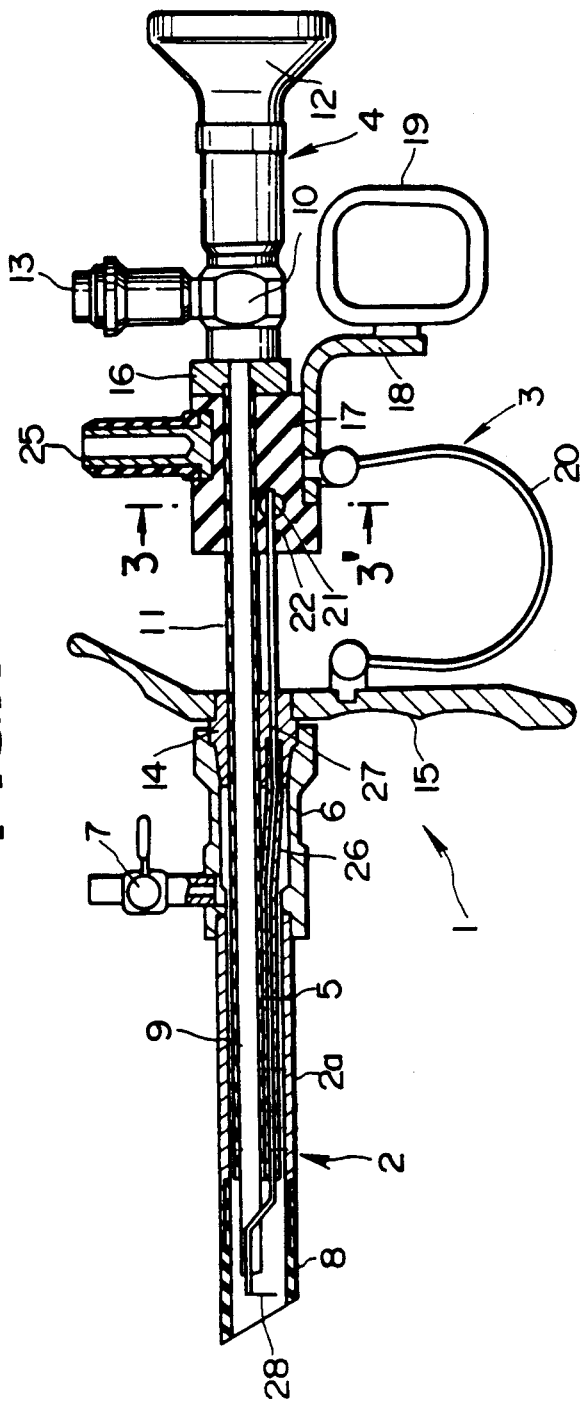
FIGS. 1 to 3 relate to the first embodiment of the present invention.
Figure 2:
Figure 3:
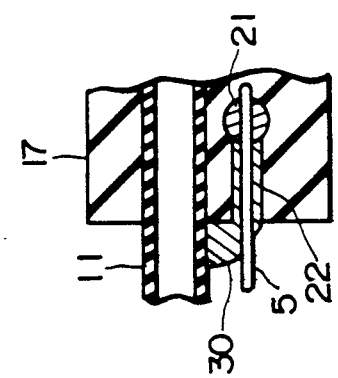

FIGS. 1 to 3 show the first embodiment of the present invention.

In this embodiment, a resectoscope apparatus 1 comprises a sheath 2, an operating part 3 removably fitted to the rear of this sheath, an optical sighting tube 4 for observation inserted through the sheath 2 from the rear of this operating part and an electrode 5 inserted through the sheath 2 from the above mentioned operating part 3.

The above mentioned sheath 2 consists of a hollow tube part 2a and a tubularly formed sheath body 6 communicating with the hollow tubular part 2a is connected and fixed to the rear end of this hollow tubular part 2a. This sheath body 6 is provided with a water feeding port 7 for injecting such liquid as an irrigating liquid. A beak tubularly formed of an insulating material is provided at the front end of the hollow tube part 2a.

The above mentioned optical sighting tube 4 consists of an insertable part 9 and a hand base part 10. This insertable part 9 is inserted and held in a guide tube 11 provided in the above mentioned operating part and formed of such electric insulating material as plastics.

By the way, the electric insulating material is such as polycarbonate (abbreviated as PC), polyacetal (polyoxymethylene abbreviated as POM), polyphenylene oxide (abbreviated as PPO), polysulfone (abbreviated as PSU), polyphenylene sulfide (abbreviated as PPS) or polyether imide (abbreviated as PEI).

A light guide and observing optical system not illustrated are inserted within the insertable part 8 and a light guide contact part 13 feeding an illuminating light to the light guide not illustrated is provided on the side of the hand base part 10. Further, an eyepiece 12 for observing an object image illuminated by the illuminating light transmitted by the light guide not illustrated and transmitted by the observing optical system not illustrated is provided at the rear end of the hand base part 10.

A sheath connecting part 14 is provided on the outer periphery near the middle part of the above mentioned guide tube 11 and is removably connected and fixed with the sheath body 6. By connecting this sheath connecting part 14 with the sheath body 6, the guide tube 11 is fixed to the sheath 2 in a fixed position. A finger hanger 15 is provided to project on the sheath connecting part 14.

On the other hand, a fixing part 16 for positioning and fixing the above mentioned optical sighting tube 4 in a fixed position is fixed and provided at the rear end of the guide tube 11. A slider 17 formed of an insulating material is loosely fitted so as to be slidable forward and rearward on the outer peripheral surface of the above mentioned guide tube 11 between this fixing part 16 and the above mentioned sheath connecting part. A finger hanging ring 19 is fixed and provided through a downward bent plate member 18 in the lower part of the slider 17. A plate spring 20 is provided between the slider 17 and the above mentioned finger hanger 15 so that the slider 17 may stand by as butted against the fixing part 16.

A columnar electrode receptacle 21 is inserted at right angles with the lengthwise direction of the guide tube 11 from the side in the middle part of the above mentioned slider 17. An electrode, inserting hole 22 provided parallel to the lengthwise direction of the guide tube 11 from the front end surface of the slider 17 passes through this electrode receptacle 21. In FIG. 3, a set screw 23 is screwed in the center in the lengthwise direction of the electrode receptacle 21 and projects at the tip into the electrode inserting hole 22. A grip 24 formed of an electric insulating material is fixed and provided at the rear end of this set screw 23. An electrode cord connecting part 25 connected to a high frequency current source not illustrated is provided in the upper part of the slider 17 and is electrically connected with the electrode receptacle 21 within the slider 17.

An electrode inserting tube 26 is provided substantially parallel below the above mentioned guide tube 11 and is fixed at the rear end to the above mentioned sheath connecting part 14. The tube path within this electrode inserting tube 26 communicates with the electrode inserting hole 27 provided in the sheath connecting part 14.

The above mentioned electrode 5 is inserted from the front end of the above mentioned electrode inserting tube 26, is inserted at the rear end into the electrode inserting hole 22 provided in the slider 17 and electrode receptacle 21 through the sheath connecting part 14 and is fixed to the electrode receptacle 21 by the tip of the set screw 23. On the other hand, a loop 28 is formed arcuately with an inside diameter slightly smaller than the inside diameter of the beak 8 of the sheath at the front end of the electrode 5 and is electrically led to the electrode receptacle 21. The electrode 5 is insulated and coated except on the loop 28 and the rear end part is inserted in the electrode receptacle 21.

In the case of using the resectoscope apparatus 1 formed as mentioned above, the electrode cord connecting part 25 is connected with the high frequency current source not illustrated through an electrode cord. Then, the sheath 2 is inserted into a body cavity, the thumb of one hand is hung on the ring 19, the remaining fingers are hung on the finger hanger 15 and the slider is advanced. With the advance of the slider 17, the electrode 5 fixed to the slider 17 will advance and the loop 28 provided at the front end of the electrode 5 will project out of the front end of the sheath 2. While observing with the optical sighting tube 4, an affected part is positioned between the loop 28 and the front end of the sheath and is fed with an electric power from the high frequency current source not illustrated. Thereafter, the pushing in the slider 17 is released. The slider 17 will be retreated rearward by the energizing force of the plate spring 20, with it, the above mentioned loop 28 will also retreat and therefore the above mentioned affected part will be able to be held between the front end part of the sheath 2 and the loop 28. The loop 28 fed with a high frequency current can burn off the held affected part.

Now, as shown in FIG. 2, when a liquid enters the electrode inserting hole 22 or forms water drops between the electrode 5 and guide tube 11, if the guide tube 11 is formed of such conductive material as a metal, the liquid will form a conductive path and an electric current will leak from the electrode receptacle 21 to the guide tube 11. However, in this embodiment, as the guide tube 11 is formed of an electric insulating material, even if the current reaches the liquid, the current will not flow further and as a result will not leak. Therefore, the current can be prevented from leaking out of the electrode inserting hole and from burning or electrically shocking the patient and operator.

Also, in this embodiment, only the guide tube 11 is formed of an electric insulating material but any or all of the sheath connecting part 14, electrode inserting tube 26 and finger hanger 15 can be formed of the electric insulating material to further elevate the safety. The insulating material may be used further for the plate member 18, finger hanging ring 19, fixing part 16 and hand base part 10 of the optical sighting tube 4.

Figure 4:
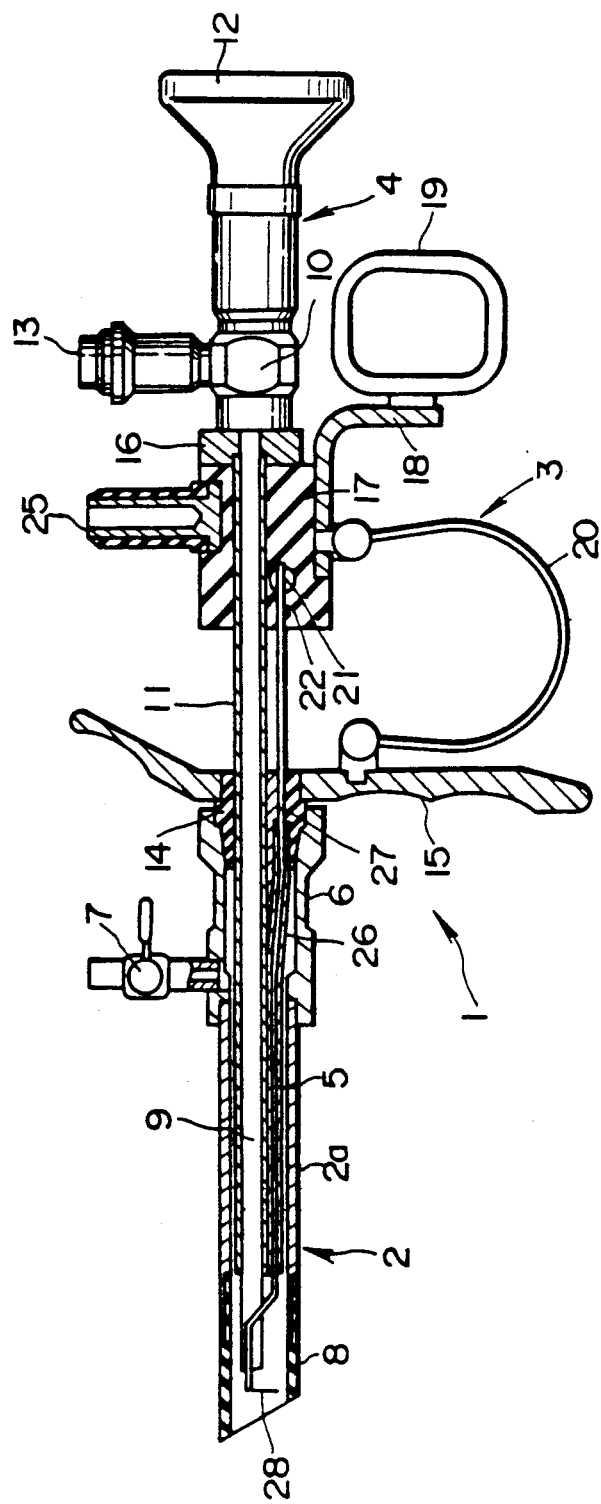
FIG. 4 relates to the second embodiment of the present invention and is an explanatory view of the entire formation of a resectoscope apparatus.
Figure 5:
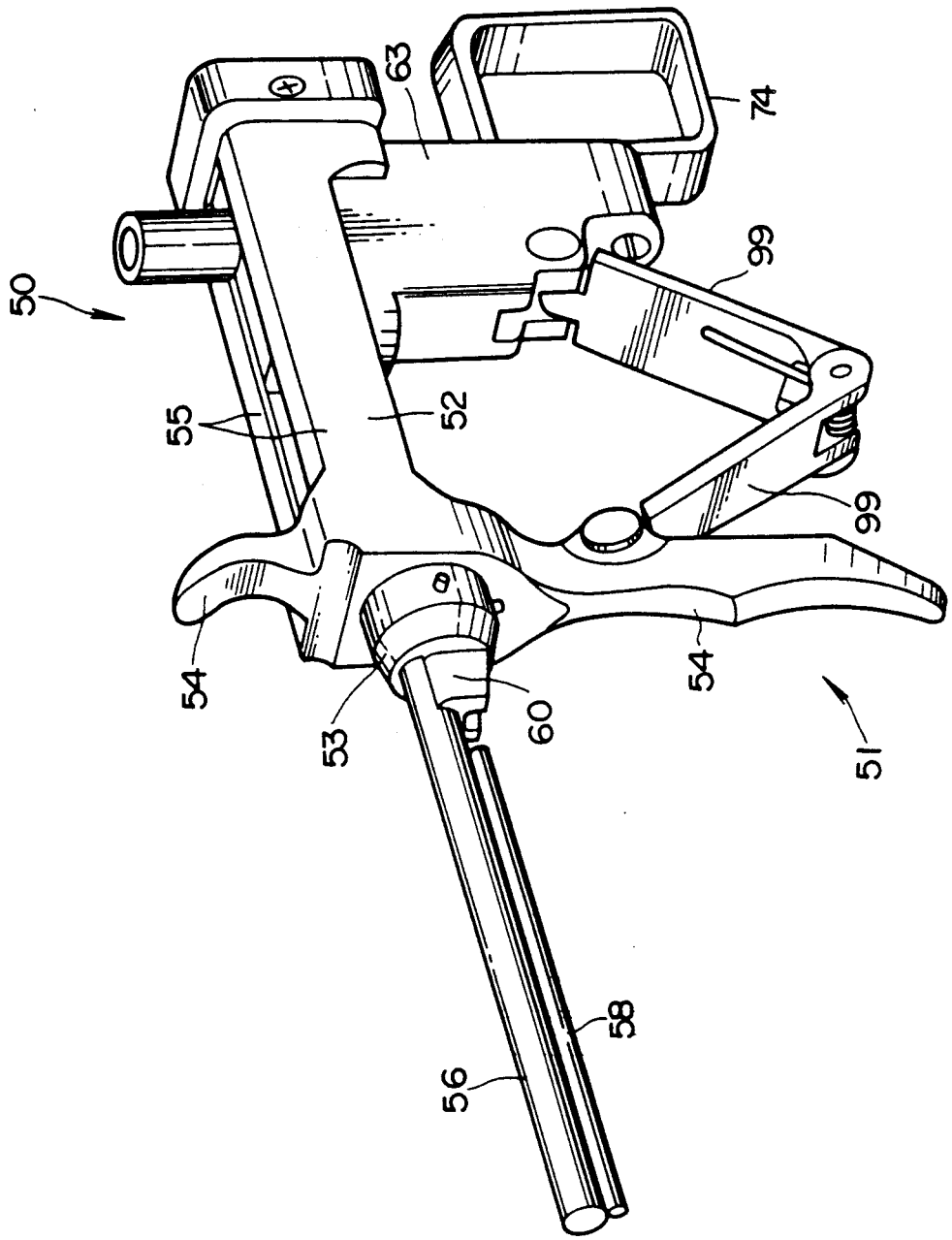
FIGS. 5 to 12 relate to the third embodiment of the present invention.

FIG. 4 relates to the second embodiment of the present invention and is an explanatory view of the entire formation of a resectoscope apparatus.

In this embodiment, instead of the guide tube 11 described in the first embodiment, the sheath connecting part 14 is formed of an electric insulating material but the other formations are the same as in the first embodiment.

By such formation as in this embodiment in case the slider is moved forward into close contact with the sheath connecting part, the electric current will be able to be prevented from leaking between the electrode contact and sheath connecting part and the same effect as in the first embodiment will be able to be obtained.

FIGS. 5 to 12 show the third embodiment of the present invention.

In this embodiment, an operating part 51 is formed of such electric insulating material as plastics by integrating a sheath connecting part 53, a finger hanger 54 and a reinforcing part 55 extended rearward of this finger hanger 54.

A resectoscope apparatus 50 of this embodiment comprises a sheath 2 of the same formation as is described in the first embodiment, an operating part 51 connected and fixed to the rear end of this sheath 2, an optical sighting tube 94 inserted from the rear of this operating part 51 and the same electrode 5 as is described in the first embodiment inserted through the sheath 2 from the above mentioned operating part 51.

The body 52 of the above mentioned operating part 51 is provided in the front part with a sheath connecting part 53 removably connecting the above mentioned sheath 2 and provided with a guide tube 56 inserted in the front part through the sheath 2. This guide tube 56 is extended rearward through the sheath connecting part 53. A finger hanger 54 is provided to project in the vertical direction of the sheath connecting part 53. In the rear of this finger hanger 54, reinforcing parts 55 are extended so as to hold the above mentioned guide tube 56. The part projecting between the reinforcing parts of this guide tube 56 is coated with an insulating pipe 57 formed of such electric insulating material as plastics. Further, the guide tube 56 forward of the sheath connecting part 53 is parallelly provided with an electrode inserting tube 58.

The above mentioned sheath connecting part 53 is provided with an electrode inserting hole 59 in front of which is formed a guide ,60 leading to the electrode inserting hole 59 an electrode not illustrated coming through the electrode inserting tube 58. On the rear inner peripheral wall of the electrode inserting hole 59, an 0-ring 61 keeping the watertightness at the time of inserting the electrode is fixed by an 0-ring presser 62 internally fitted as by snap fitting.

Figure 8:
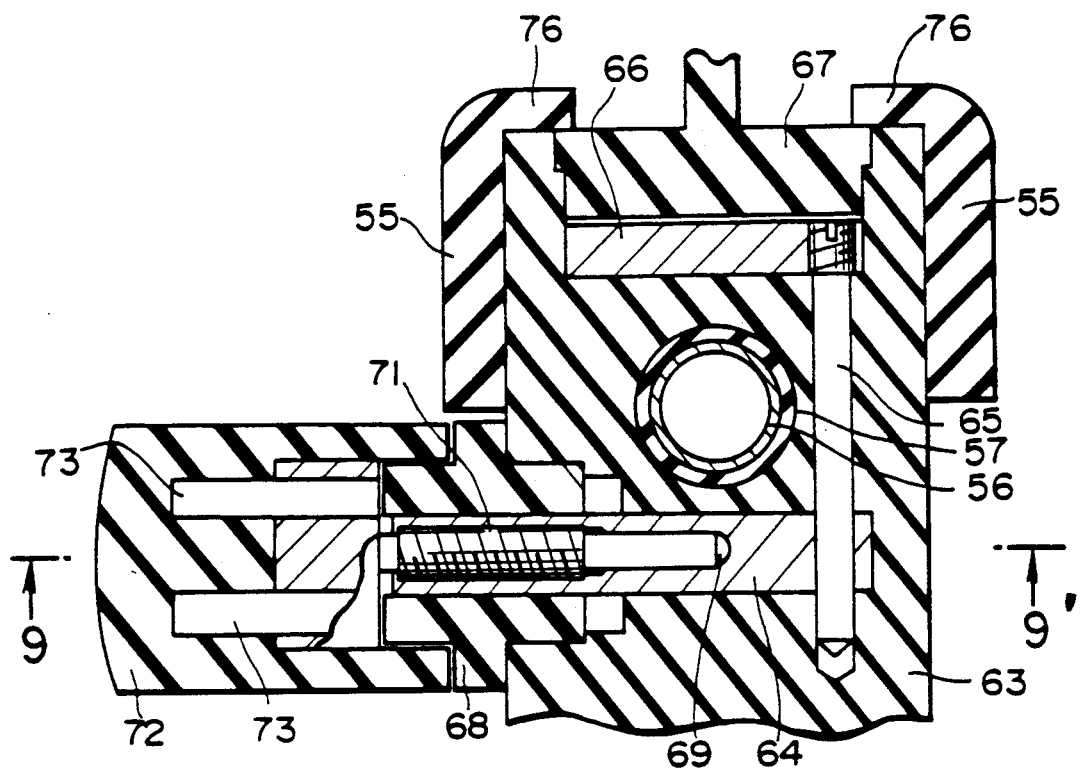
Figure 9:
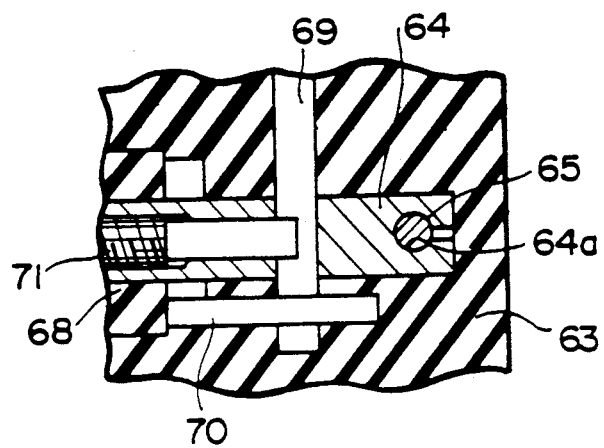

The insulating pipe 57 coating the above mentioned guide tube 56 is inserted through a guide tube inserting hole 75 provided in a slider 63 formed of an insulating material so that the slider 63 may be slidable forward and rearward. Within this slider 63, such columnar electrode receptacle 64 as is shown in FIG. 8 is inserted from the side. This electrode receptacle 64 is provided in the tip part with a slit hole 64a provided with a slit. The electrode receptacle 64 is fixed to the slider by pressing an elongate fixing pin 65 inserted from above the slider 63 into this slit hole 64a. The fixing pin 65 is provided on the head with a screw screwed into the electrode cord connecting part 66 secured to the upper part of the slider 63 so that the electrode receptacle 64 and electrode cord connecting part 66 may be electrically connected with each other. The electrode cord connecting part 66 is prevented by a cap made of an electric insulating material from being exposed out.

The above mentioned slider 63 is provided on the front end surface with an electrode inserting hole 69 passing through the above mentioned electrode receptacle 64 and provided in the end part with a positioning pin 70 butting against it the end of the electrode 5 inserted into this electrode inserting hole 69 to position the electrode 5. A set screw 71 is screwed in the center axis of the electrode receptacle 64 to fasten and fix the electrode 5 at the rear end with the tip of this set screw 71. A grip 72 formed of an insulating material is secured to the head of this set screw 71 and pins 73 are inserted to reinforce the securing part. A cap 68 formed of an electric insulating material is provided between the grip 72 of the above mentioned electrode receptacle 64 and the slider 63.

Further, in the lower part of the slider 63, a finger hanging ring 74 formed of plastics or the like is rotatably provided by snap fitting.

The distance between the reinforcing parts 55 is made somewhat larger than the width of the slider 63. The reinforcing parts 55 are bent in the upper part as shown in FIG. 8 to form ribs 76 to elevate the bending rigidity.

An optical sighting tube connecting member 77 formed of such metal as stainless steel is provided with an optical sighting tube inserting hole 78 in which the above mentioned insulating pipe is inserted and an optical sighting tube 94 is to be inserted from the rear. On the inner peripheral surface of this inserting hole 78, an O-ring 79 is fixed by a nut 80 to keep the watertightness at the time of inserting the optical sighting tube 94. Further, an O-ring 81 keeping the watertightness between the above mentioned insulating pipe 57 and inserting hole 78 is provided.

Figure 10:
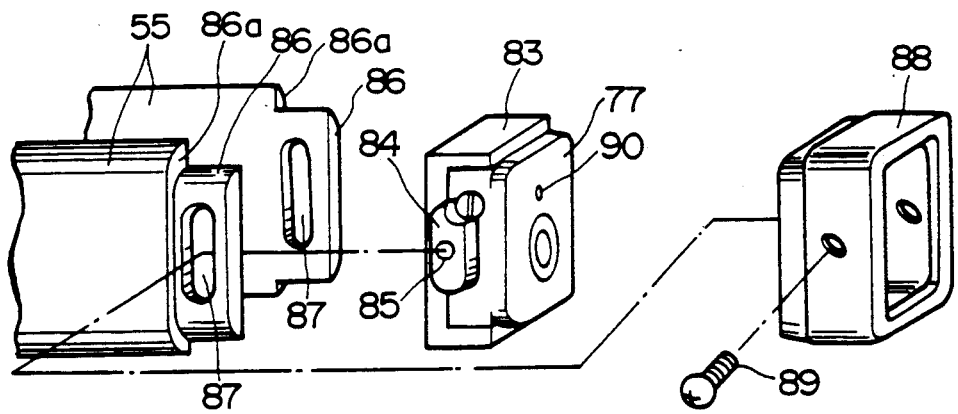

In FIG. 10, an insulating plate 83 formed to be channel-shaped of an electric insulating material is provided on the surface on the slider side of the optical sighting tube connecting member 77. The lateral width of the optical sighting tube connecting member 77 is made the same as the distance between the reinforcing parts 55 and elliptic projections 84 are provided on both side surfaces of the optical sighting tube connecting member 77. Connecting parts 86 formed to be smaller in the diameter by steps 86a are provided at the rear ends of the reinforcing parts 55. Elliptic fitting holes 87 in which the above mentioned projections 84 can be respectively fitted are provided in these connecting parts 86. In fitting the projections 84 into these fitting holes 87, the holes are pushed and expanded outward by utilizing the resiliency of the reinforcing parts 55.

After the optical sighting tube connecting member 77 is fitted to the reinforcing member 77, a ring 88 formed of an electric insulating material is fitted to the connecting parts 86 of the reinforcing parts 55 and is fixed by screwing screws 89 into screw holes 85 of the projections 84. As the reinforcing parts 55 are thereby prevented from expanding outward, the optical sighting tube connecting member 77 is fixed to the reinforcing parts 55.

Figure 11:
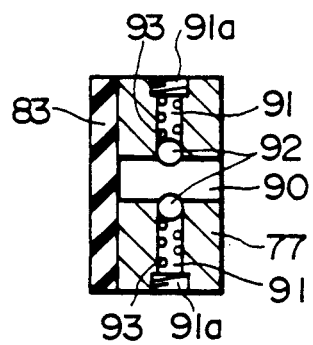
Figure 12:
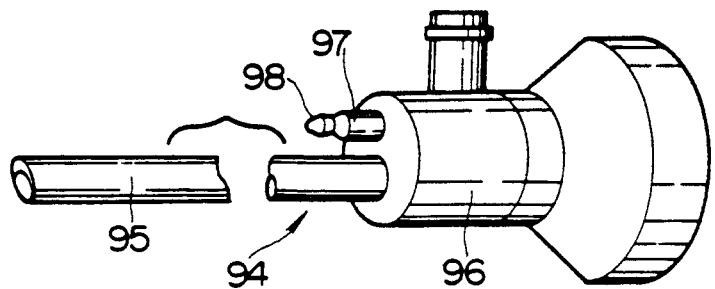

In FIGS. 11 and 12, the optical sighting tube 94 connecting mechanism shall be explained.

A connecting pin inserting hole 90 is provided as directed forward on the rear end surface of the above mentioned optical sighting tube connecting member 77 and a hole 91 passes at right angles with this connecting pin inserting hole 90. The inside diameter of the hole 91 in the position in which this hole 91 and inserting hole 90 communicate with each other is made a little smaller than the inside diameter of the hole 91 on the outside so that the metal balls 92 inserted from outside may stand by in these positions as partly projected into the connecting pin hole 90. These metal balls 92 are inserted into the hole 91 and are fixed by coil springs 93 energized by screws 91a screwed into the hole 91.

On the other hand, on the front end surface of the hand base part 96 of the optical sighting tube 94, a connecting pin 97 is provided to project forward. When the insertable part 95 of the optical sighting tube 94 is inserted into the above mentioned optical sighting tube inserting hole 78, this connecting pin 97 will be inserted into the above mentioned connecting pin inserting hole 90. The connecting pin 97 is provided on the tip part peripherally with a groove 98 in which the metal balls 92 energized by the above mentioned coil springs 93 are engaged to connect and fix the operating part 51 and optical sighting tube 94 with each other.

Figure 6:
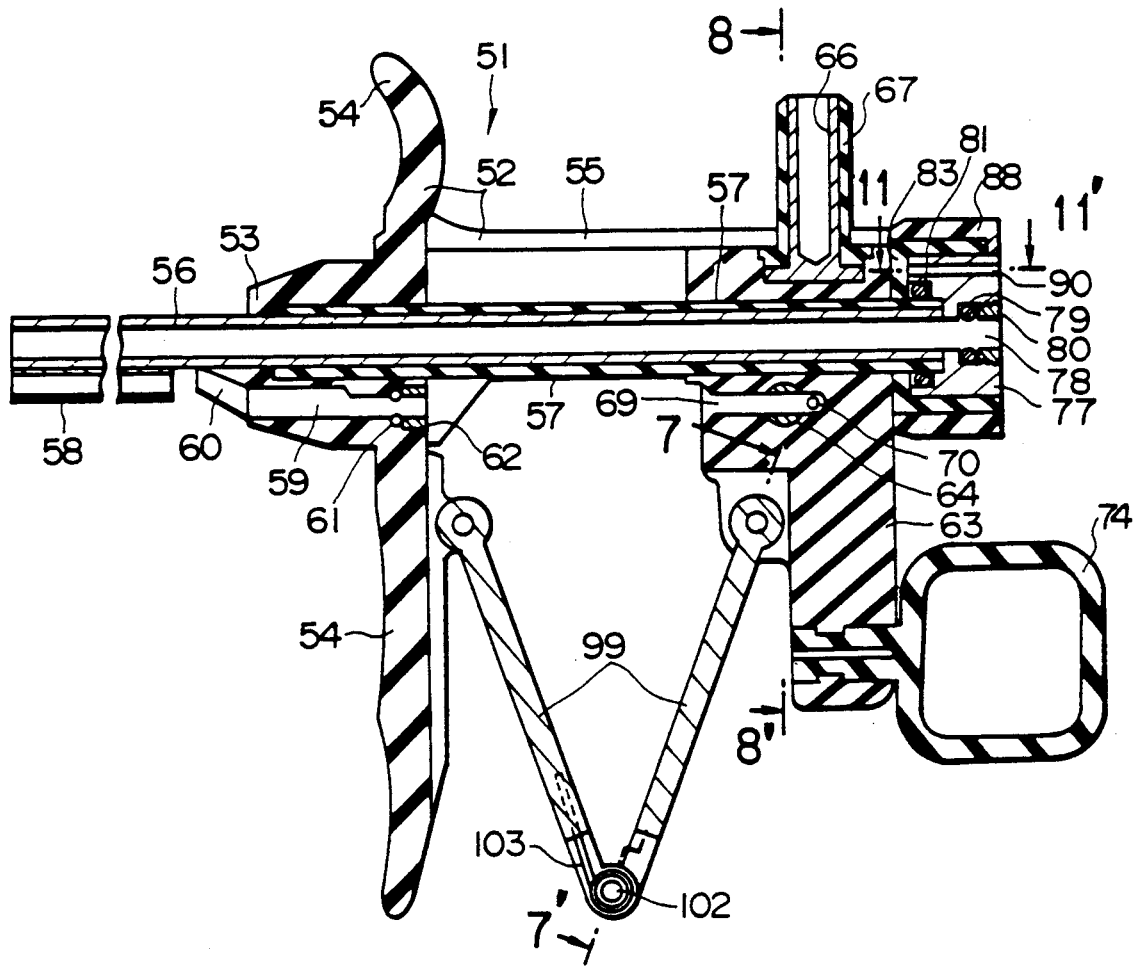
Figure 7:
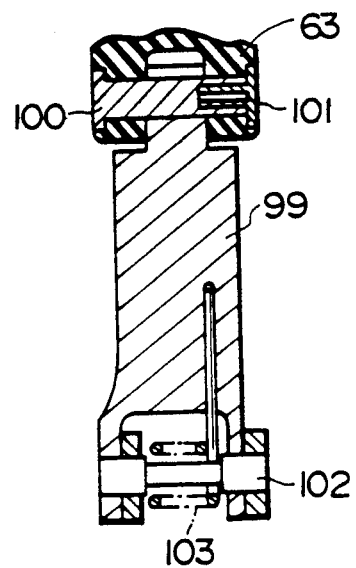

In FIG. 6, the finger hanger 54 and slider 63 are provided with link plates 99. The connecting part of this link plate 99 with the finger hanger 54 and the connecting part of the link plate 99 with the slider 63 are rotatably fitted by pressing a slit pin 101 into a set pin 100. The set pin 100 and slit pin 101 may be made of a metal or such electric insulating material as plastics.

The above mentioned link plates 99 are rotatably connected with each other by a pin 102 provided with a twisted spring 103. The slider 63 is energized by the action of the link plates 99 and twisted spring 103 so as to stand by in the rear of the operating part 51. That is to say, when the thumb is put into the finger hanging ring 74 and the other fingers are hung on the finger hanger 54, if the thumb is pushed out forward, the slider 63 will move forward but, if the force of the thumb is released, the slider 63 will be returned rearward by the energizing force of the twisted spring 103.

As the part on which the slider 63 slides of the guide tube 56 formed of a metal is coated with the insulating pipe 57 formed of such electric insulating material as plastics as in the above, the leaking electric current tending to flow from the liquid having entered the electrode inserting hole 69 or from the water drops located between the insulating pipe 57 and electrode inserting hole 69 can be prevented by the insulating pipe from flowing to the guide tube 56. The sheath connecting part is also formed of an electric insulating material and, in case the slider is moved forward into close contact with the sheath connecting part, the electric current will be able to be prevented from flowing between the electrode contact and sheath connecting part and the patient and operator will be able to be prevented from being burned or electrically shocked.

In this embodiment, since the guide tube 56 can be formed of a metal high in the strength, there are advantages that the thickness of the guide tube 56 can be made smaller to make the space within the sheath 2 larger and the fed amount of the irrigating liquid flowing through this space can be increased.

Figure 13:
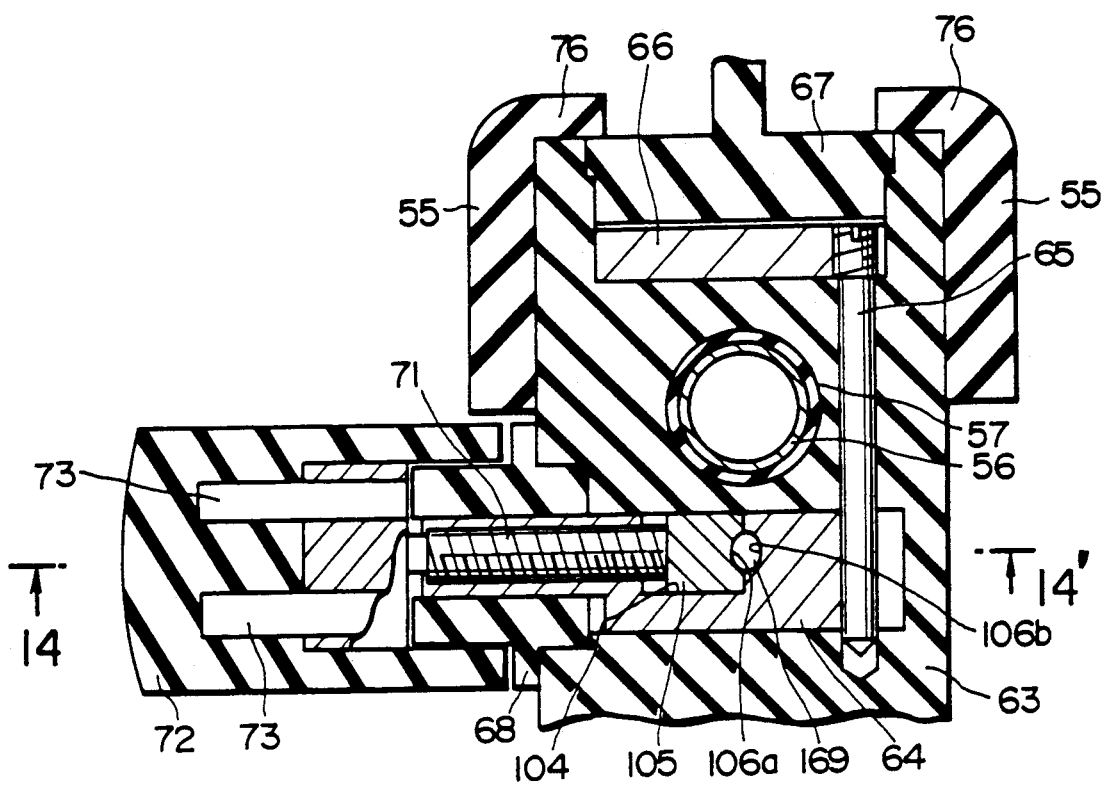
FIGS. 13 and 14 relate to the fourth embodiment of the present invention.
Figure 14:
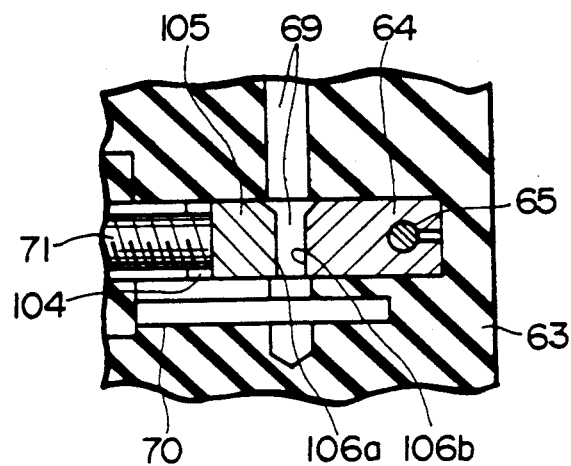
Figure 15:
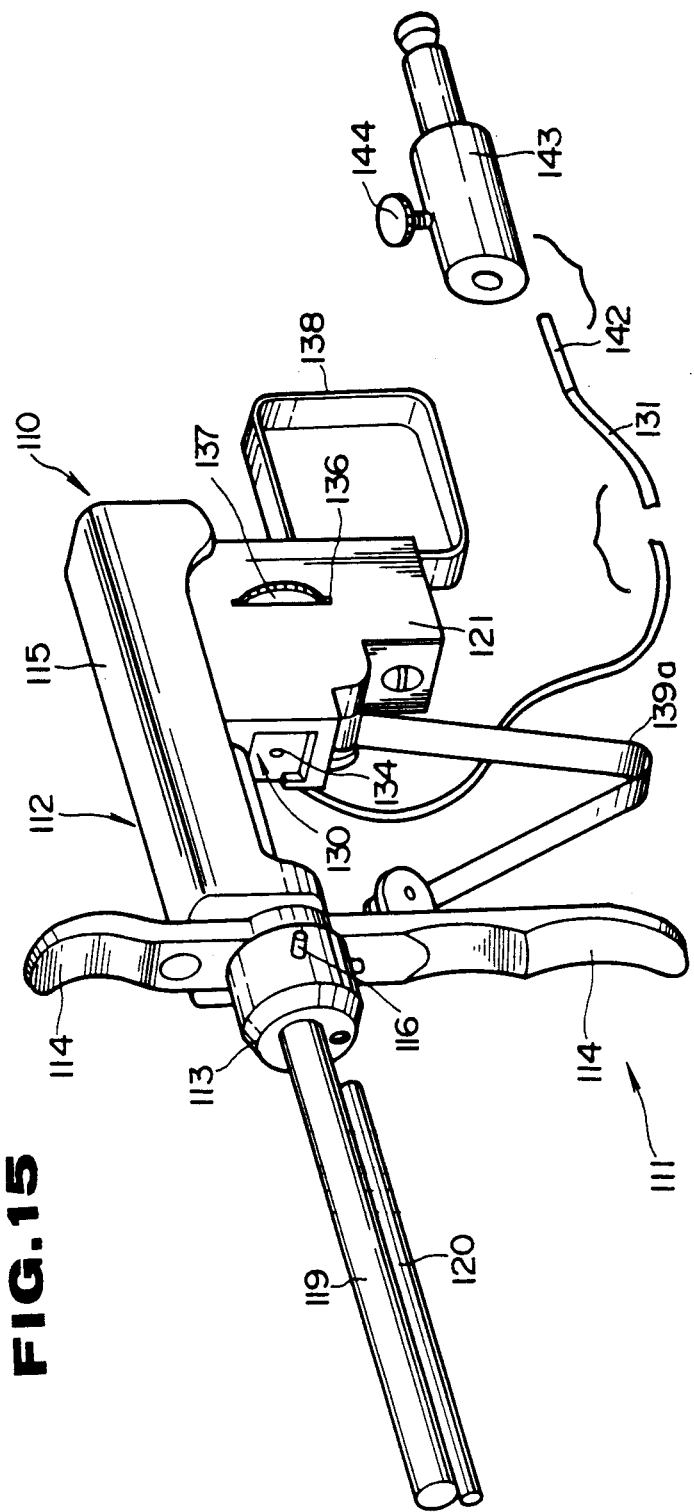
Figure 16:
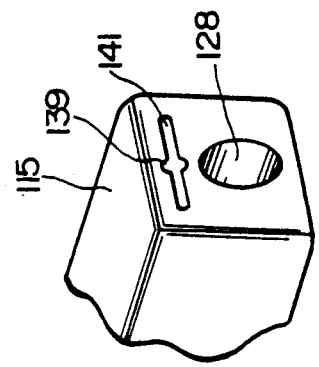

FIGS. 13 and 14 show the fourth embodiment of the present invention.

This embodiment is the same as the third embodiment except in the formation of the electrode receptacle.

On the upper surface of the electrode receptacle 64 of this embodiment, an incision 104 is provided in the lengthwise direction of the guide tube 56. Within this incision 104, an electrode presser 105 is provided slidably in the direction substantially at right angles with the lengthwise direction and is pressed by the tip of the set screw 71 screwed into the electrode 64 so as to contact the side surface forming the incision 104. Arcuate grooves 106b and 106a are provided on the side surfaces respectively on the electrode receptacle 64 side and the electrode presser 105 side in contact with each other. The space formed by these grooves 106a and 106b communicates with the electrode inserting hole 69. By the way, the groove 106a on the electrode presser 105 side is formed to be shallower than the radius of the shaft part of the electrode.

The other formations are the same as in the third embodiment.

In this embodiment, in fitting the electrode 5 to the operating part 51, with the set screw 71 loosened, the electrode 5 is inserted into the electrode inserting tube 58 from the front end and is led to the electrode inserting hole 69 of the slider 63 through the electrode inserting hole 59 of the sheath connecting part 53. The electrode 5 is inserted into the electrode inserting hole 69 to butt against the positioning pin 70 while pushing the electrode presser 105 outward and then the set screw 71 is screwed in to press and move the electrode presser 105 to the electrode inserting hole 69 side so that the electrode 5 may be held and fixed by the electrode receptacle 64 and electrode presser 105.

In this embodiment, as the electrode 5 is held by the groove 106a of the electrode presser 105 and the groove 106b of the electrode receptacle 64, as compared with the case of directly fastening the electrode 5 with the set screw 71, there is an advantage that no deformation will be produced.

The other formations and effects are the same as in the third embodiment.

FIGS. 15 to 20 show the fifth embodiment of the present invention.

In this embodiment, a body 112 of an operating part 111 of a resectoscope apparatus 110 comprises a sheath connecting part 113, finger hanger 114 and case part 115 and is integrally molded of such electric insulating material as plastics.

The above mentioned sheath connecting part 113 is provided symmetrically on the right and left with connecting pins 116 for connecting the sheath 2 and is provided within with an optical sighting tube inserting hole 117 and an electrode inserting hole 118. A guide tube 119 inserting the optical sighting tube 94 is internally fitted on the front side of this optical sighting tube inserting hole 117 so that the optical sighting tube inserting hole 118 and the inner path of the guide tube 119 may communicate with each other. An electrode inserting tube 120 is secured parallel to the guide tube 119 so that the electrode 5 inserted through the electrode inserting tube 120 may be led to the above mentioned electrode inserting hole 118.

The above mentioned sheath connecting part 113 is provided in the rear with a case part 115 within which a slider 121 formed of such electric insulating material as plastics is loosely fitted so as to be slidable forward and rearward. This slider 121 is provided with an insulating pipe inserting hole 122 through which is slidably inserted an insulating pipe 123 communicating with the above mentioned guide tube 119 and made of such electric insulating material as plastics. This insulating pipe 123 is externally fitted at the front end with an O-ring presser 124 made of such electric insulating material as the same plastics, internally fitted to the rear of the sheath connecting part 113 and further fixing an O-ring 126 provided on the inner periphery of the opticial sighting tube inserting hole 117 of the sheath connecting part 113 and an O-ring 127 provided on the inner periphery of the electrode inserting hole 118. The second guide tube or insulating pipe 123 is internally fitted at the rear end in an optical sighting tube inserting hole 128 provided in the rear of the case part 115 and is pressed against the O-ring presser 124 side by an annular nut 129 screwed in from the rear.

In this information, when the nut 129 is removed, the insulating pipe 123, O-ring presser 124, O-rings 126 and 127 and slider 121 will be able to be disassembled from the body 112 to be easily replaced.

The above mentioned slider 121 is provided with an electrode fixing part 130 slidably in the lengthwise direction. This electrode fixing part 130 is formed of such electric insulating material as plastics on the periphery of an electrode receptacle 132 fitted with an electrode cord 131 and has a set screw 133 screwed in from the side. This set screw 133 projects at the tip into an electrode inserting hole 134 provided in the lengthwise direction and a grip 133a made of an electric insulating material is secured to the head of the set screw 133. Further, this electrode fixing part 130 is provided with a positioning screw 135 projecting rearward and screwed into a positioning ring 137 within a positioning ring inserting groove 136 provided in the slider 121. That is to say, the electrode fixing part 130 comprises an electrode 154 formed integrally with an electrode part 152 and cord part 152, an optical sighting tube inserting part 155 in which an optical sighting tube 94 is inserted and connected, a slider 156 sliding the above mentioned electrode 154 forward and rearward and a body 157.

Further, a rigid part 158 provided at the rear end of the above mentioned cord part 153 is to be removably fixed to a plug 160 electrically and mechanically connected with a high frequencY current source not illustrated. A holding part 161 formed columnarly of an electric insulating material of this plug 160 is provided on the end surface with a connecting hole 162 in which the above mentioned rigid part 158 is to be inserted. Further, a screw 163 fixing the inserted rigid part 158 is screwed into the peripheral surface of the holding part 161.

Figure 22:
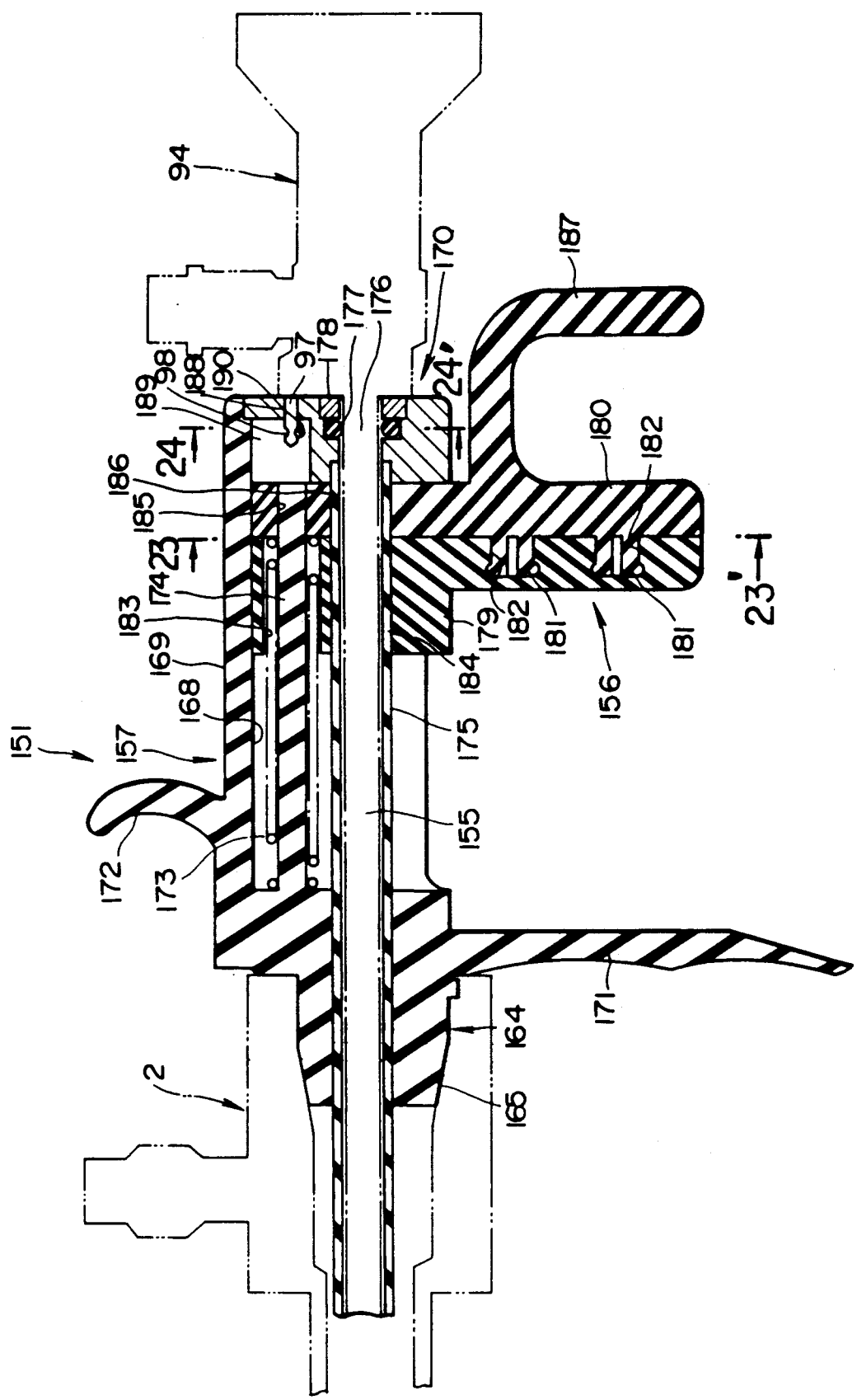
Figure 23:
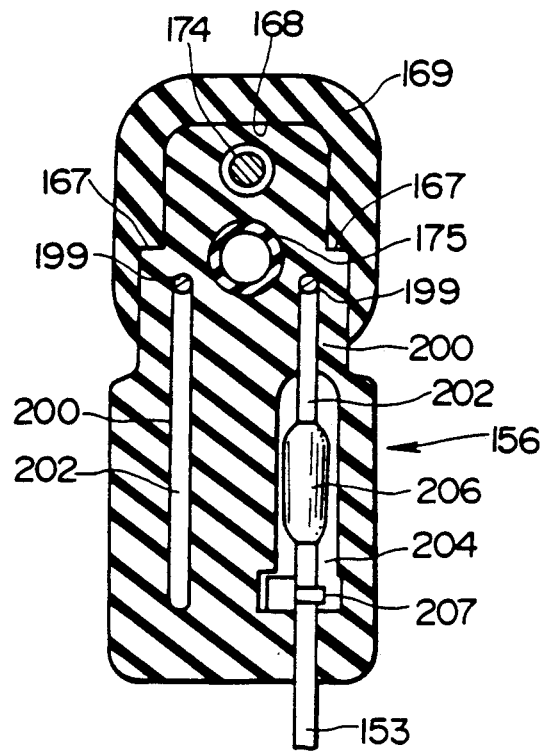
Figure 24:
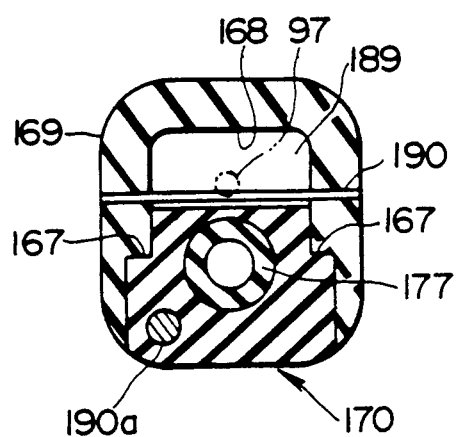

In FIG. 22, a sheath connecting part 164 is formed in front of the body 157 forming the operating part 151 and is provided in front with a tapered part 165 smaller in the diameter forward and provided in the rear with a pin 166 to project so that the sheath connecting part 164 may be connected with the sheath 2 removably and watertightly by this pin 166 and the above mentioned tapered part 165.

The sheath connecting part 164 is provided in the rear with a cover 169 having a substantially square cross-section and extending rearward and is provided below this cover 169 with a groove 168 in the lengthwise direction. An optical sighting tube connecting part 170 is provided in the rear of this groove 168. Further, between the sheath connecting part 164 and groove 168, a lower finger hanger 171 is provided downward so that the middle finger and third finger may be hung in case the operating part 151 is held with one hand and an upper finger hanger 172 on which the forefinger may be hung is provided to project upward above the cover 169. Within the above mentioned groove 168, a spring shaft 174 is provided to extend rearward from the sheath connecting part 164 side and is externally fitted with a coil spring 173 as wound. The sheath connecting part 164, tapered part 165, pin 166, cover 169, lower finger hanger 171, upper finger hanger 172 and spring shaft 174 are formed of plastics and are integrally molded as a molding.

A guide tube 175 formed of such electric insulating material as plastics and passed through the above mentioned sheath connecting part 164 is inserted below the spring shaft 174 within the groove 168 and is internally fitted at the rear end in an optical sighting tube inserting hole 176 provided in the above mentioned optical sighting tube connecting part 170 so that the tube path of the guide tube 175 and the optical sighting tube inserting hole 176 may communicate with each other. An O-ring 177 is fixed by an 0-ring presser 178 on the inner periphery of this optical sighting tube inserting hole 176. The optical sighting tube 94 as kept watertight is inserted through the guide tube 175 from the optical sighting tube inserting hole 176 and the tip part of the optical sighting tube 94 can be led to the tip part of the operating part 151.

A slider part 156 is provided within the above mentioned groove 168 and consists of a slider front part 179 and slider rear part 180 formed of plastics. The upper contours of the slider front part 179 and slider rear part 180 are the same as the shape of the groove 168. A spring hole 183 passes through this slider front part 179 and a shaft hole 185 passes through the slider rear part 180 so as to communicate with this spring hole 183. Further, below the spring hole 183 and shaft hole 185 is provided a guide tube hole 184 so as to pass through the slider front part 179 and slider rear part 180. The above mentioned spring shaft 174 is inserted through this shaft hole 185. The coil spring 173 is inserted through the spring hole 183 provided in the slider front part 179 and is energized to press the front end surface of the slider rear part 180. In the guide tube hole 184, the guide tube 175 slidably supports the slider part 156.

The above mentioned slider front part 179 is provided on the rear end surface with holes 182. On the front end surface of the slider rear part 180 opposed to the rear end surface of the above mentioned slider front part 179, snap fits 181 are provided to project in the positions corresponding to the holes 182 and are made integral with the holes 182 by being engaged with the holes 182.

Further, a thumb hanger 187 preventing the thumb hung on the rear surface of the slider rear part 180 from slipping in case the operating part 151 is held with one hand is provided to extend from the rear end surface of the slider rear part 180. When pushed forward with the thumb, this slider part 156 will be able to forward against the force of the above mentioned coil spring 173 but, when the force of the thumb is released, the slider part 156 will contact the front end surface of the optical sighting tube connecting part 170 due to the energizing force of the coil spring 173.

A pin hole 188 inserting the connecting pin 97 of the optical sighting tube 94 shown in FIG. 12 is provided above the optical sighting tube inserting hole 176 on the rear end surface of the above mentioned optical sighting tube connecting part 170 and passes through a space 189 provided within the optical sighting tube connecting part 170. Within this space 189, a piano wire 190 is set substantially at right angles with the lengthwise direction in front of the pin hole 188 so that, when the connecting pin 97 is inserted into the pin hole 188, the piano wire 190 will engage with the groove 98 provided in the connecting pin 97 to removably connect the optical sighting tube 94 to the operating part 151.

Figure 25:
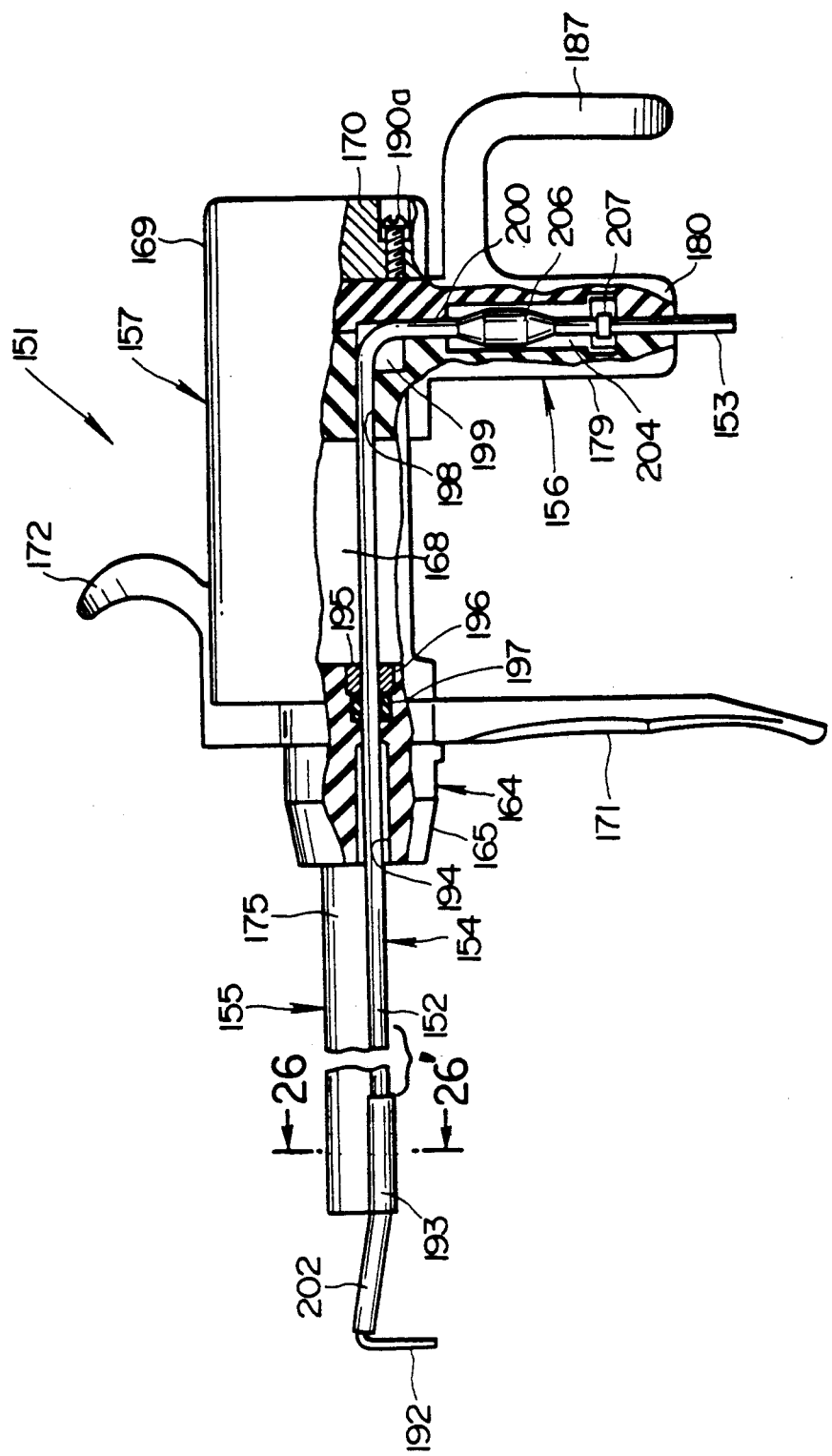
Figure 28:
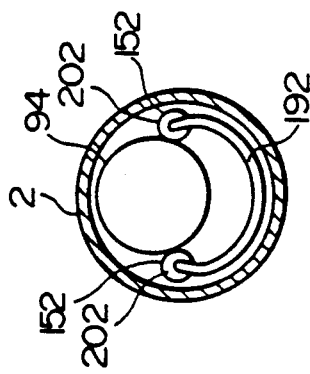

As shown in FIG. 25, a screw 190a is screwed in from the rear end surface of the optical sighting tube connecting part 170 so that the position of standing by within the groove 168 of the slider part 156 may be adjusted. The tip part projects into the groove 168 to contact the rear end surface of the slider part 156.

Figure 26:
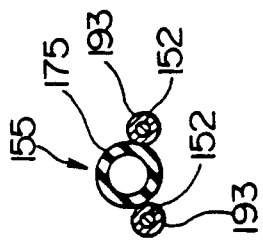

In FIGS. 25 and 26, the electrode part 152 of the above mentioned electrode 154 is kept inserted through guide pipes 193 provided on both sides of the lower part of the above mentioned guide tube 175, passes slidably through the sheath connecting part 164 and is then bent downward within the slider part 156. In the electrode part 152, as in FIG. 27, a current flowing wire 191 is inserted through a stainless steel pipe 201 which is further electrically insulated and coated on the periphery with a Teflon tube 202. The front end part of the electrode part 152 projects forward on the right and left from the front end of the guide tube 175 and the wire 191 is exposed from the electric insulating part. This exposed wire 191 forms a loop 192 of a radius somewhat smaller than the inside diameter of the sheath 2 so as to resect tissues within a body when a high frequency current is passed.

Figure 27:
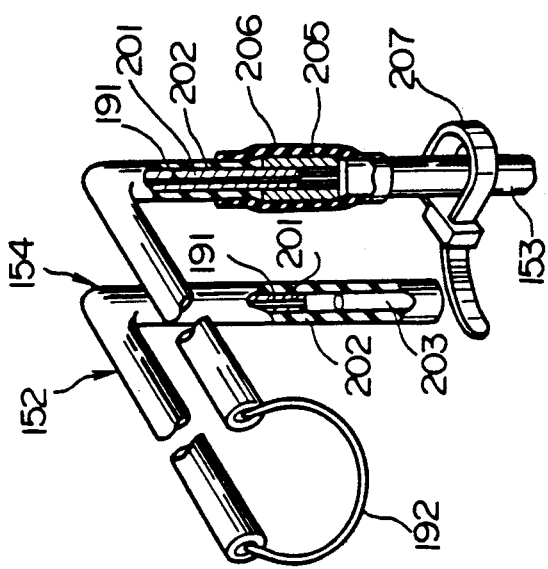

The electrode part 152 is inserted through inserting holes 194 and 0-ring holes 195 communicating with the inserting holes 194. Each 0-ring hole 195 is provided with an 0-ring 197 fixed by an 0-ring presser 196 so as to keep watertightness in case the electrode part 152 slides forward and rearward. The electrode part 152 is further inserted through electrode holes 198 provided in the slider front part 179, is then bent downward within spaces 199 provided on the contact surface of the slider front part 179 and slider rear part 180 and is led to grooves 200 provided on the contact surface of the slider front part 179 and slider rear part 180. The end part on one side of the electrode part 152 is sealed with plastics 203 within the groove 200 as shown in FIG. 27. The end part on the other side of the electrode part 152 is pressed and connected with a calking pipe 205 as electrically connected with the end part of the cord part 153 within a space 204 provided on the contact surface of the slider front part 179 and slider rear part 180 from the groove 200 and is electrically insulated and coated with a thermocontracting tube 206 on the periphery of the calking pipe 205. In the lower part of the space 204, a clamp 207 is wound on the cord part 153 lest the cord part 153 should be pulled down.

As in the above, as the guide tube 175 and sheath connecting part 164 are formed of such electric insulating material as plastics, a leaking current can be prevented from flowing to the guide tube 175 and sheath connecting part 164 and, as the electrode 154 and slider part 156 are integrally assembled, the clearance between the electrode hole 198 and electrode part 152 can be made smaller than in the formation in which the electrode is fitted and removed and, as required, this clearance can be filled with a binder or the like so that the leaking current itself from the electrode hole 198 may be kept minimum.

Figure 29:
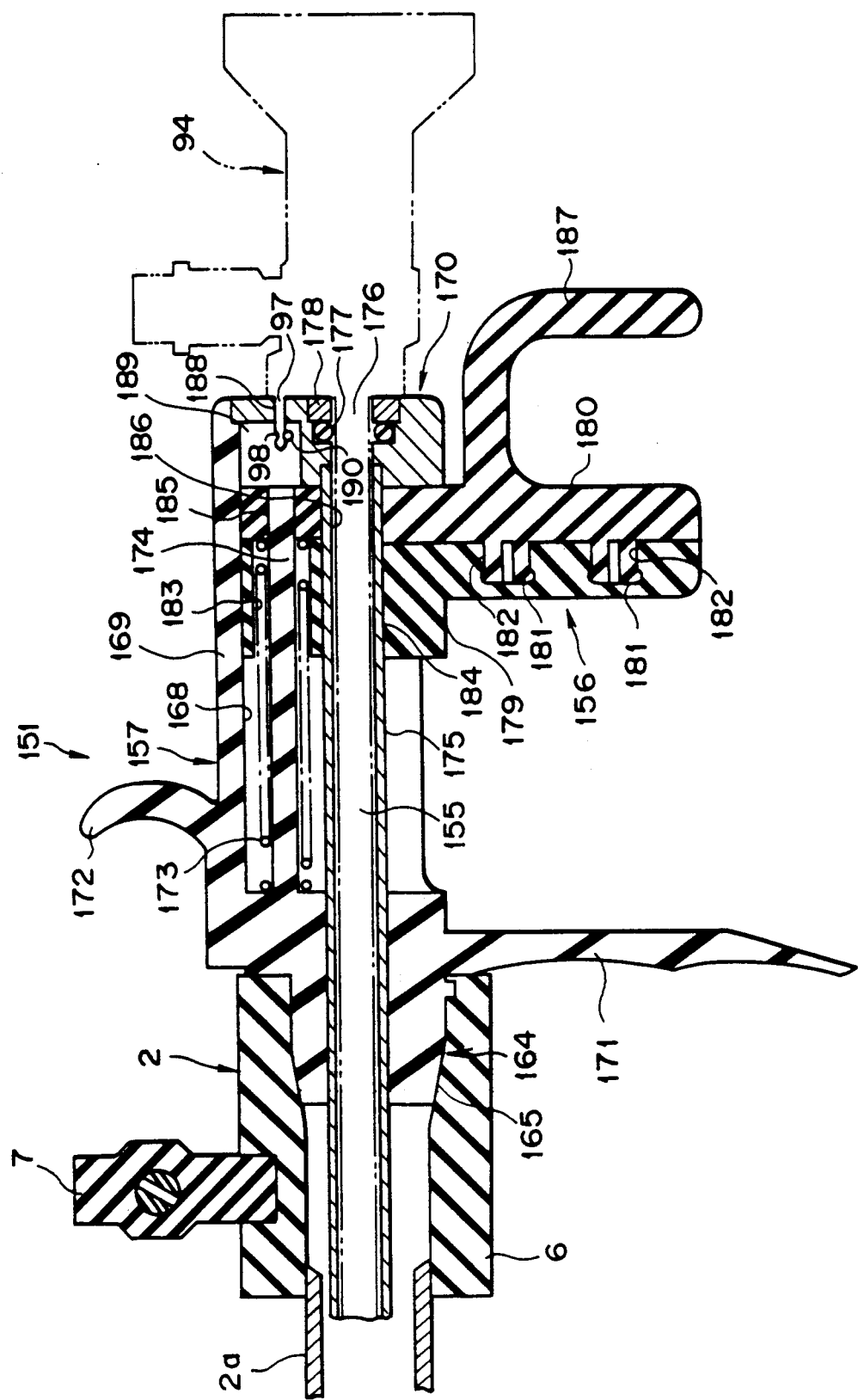
FIG. 29 relates to the seventh embodiment of the present invention and is a sectioned view of a resectoscope apparatus having a sheath connecting part formed of an electric insulating material.
Figure 30:
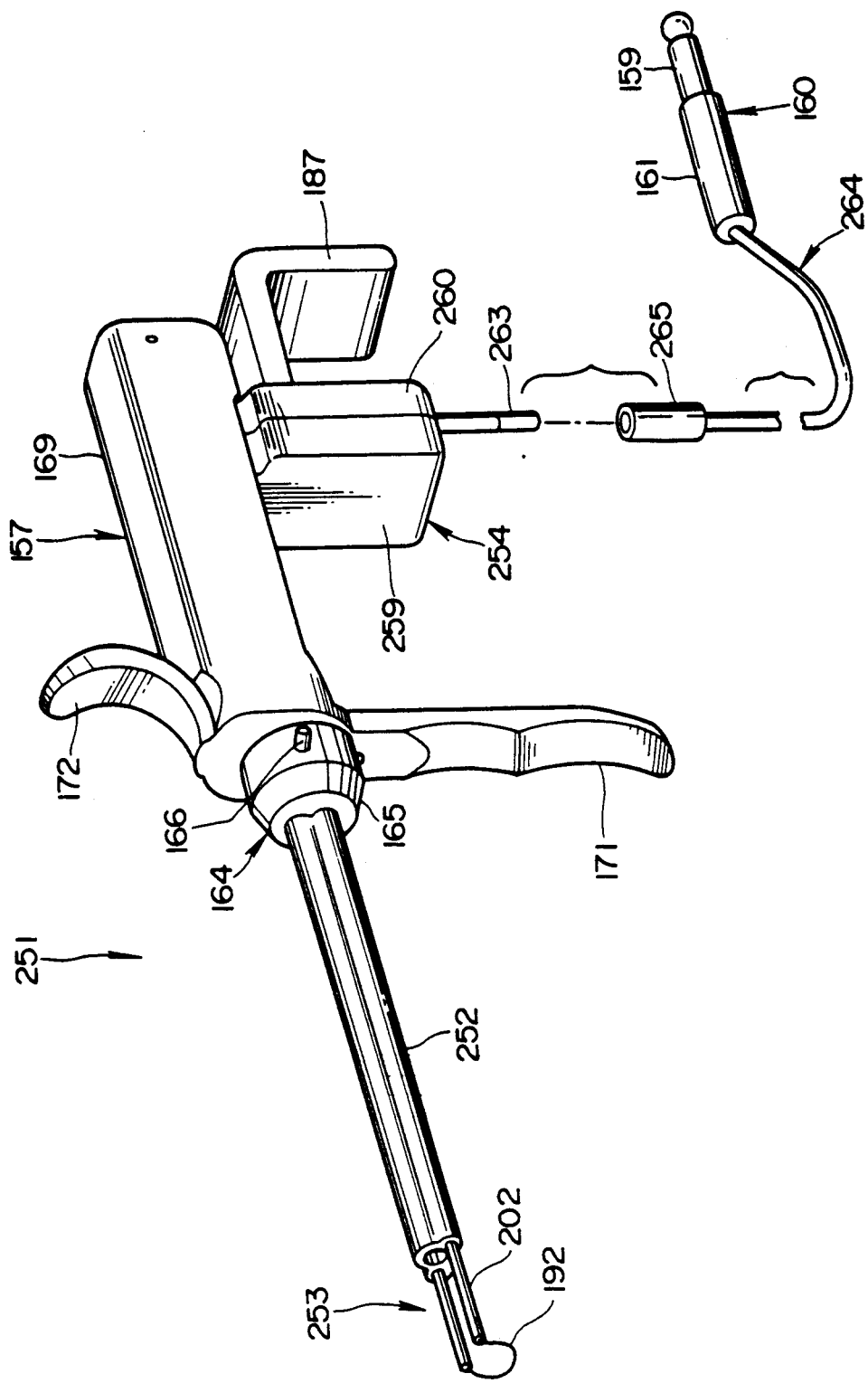
Figure 34:
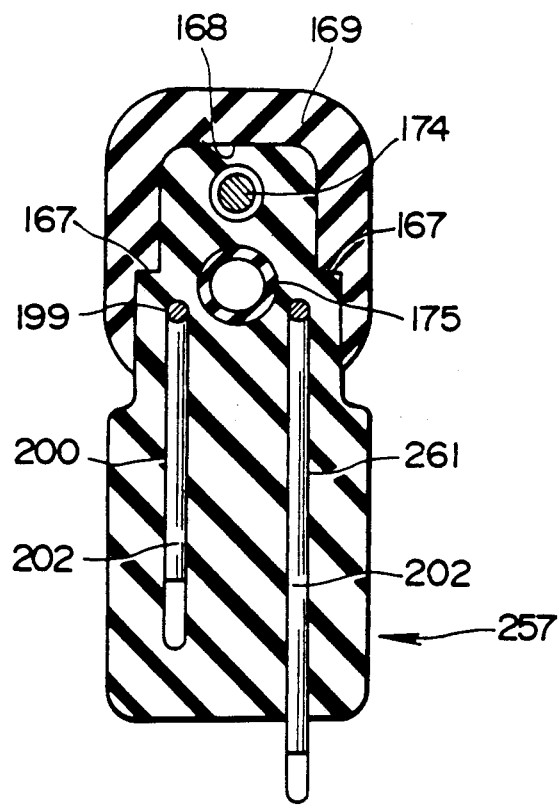
Figure 35:
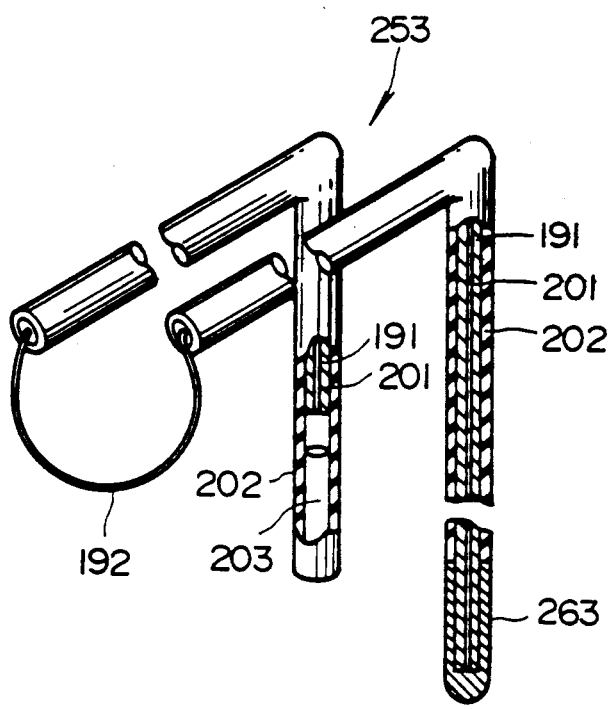
Figure 36:
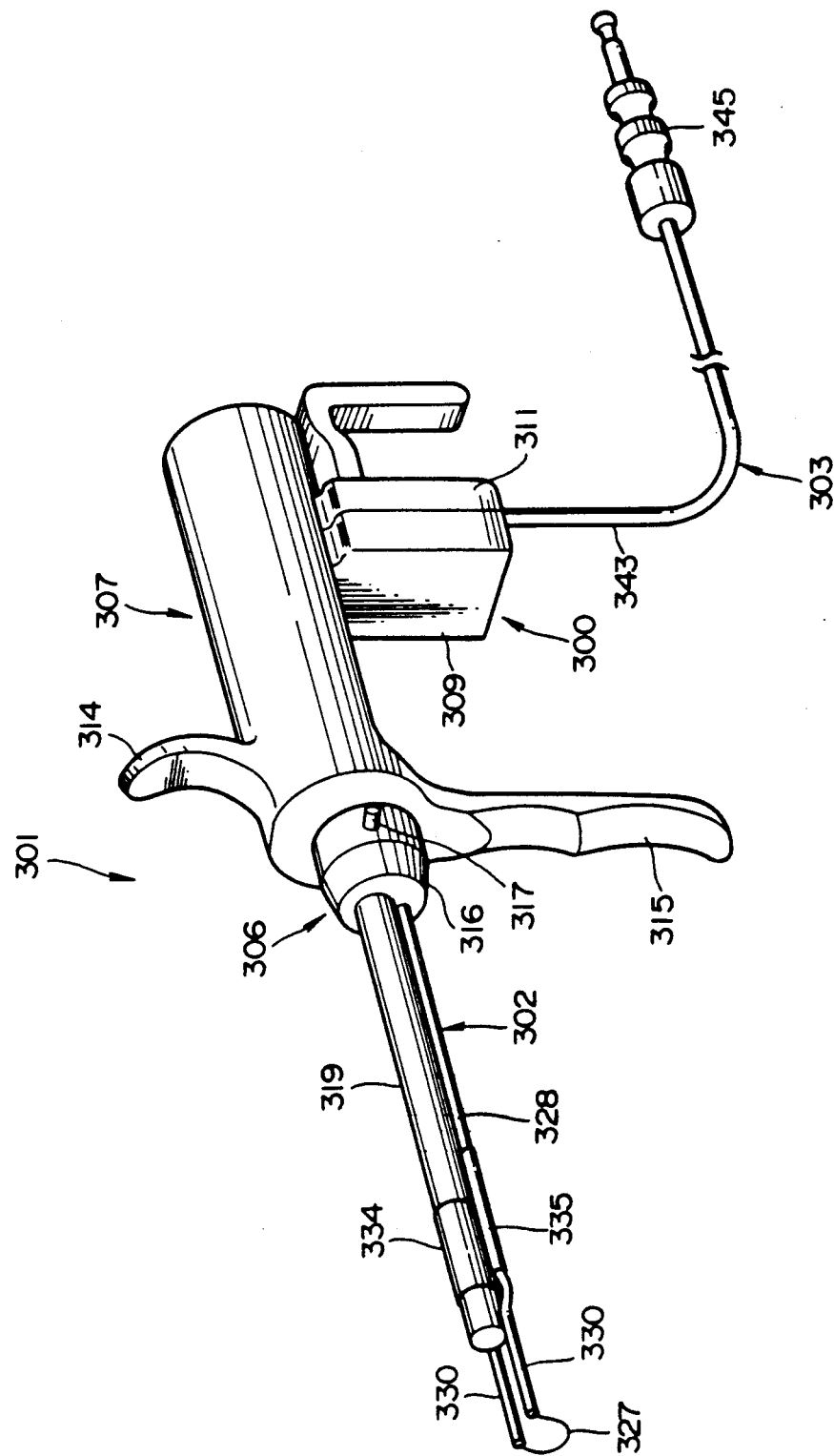
FIGS. 36 to 40 relate to the ninth embodiment of the present invention.
Figure 37:
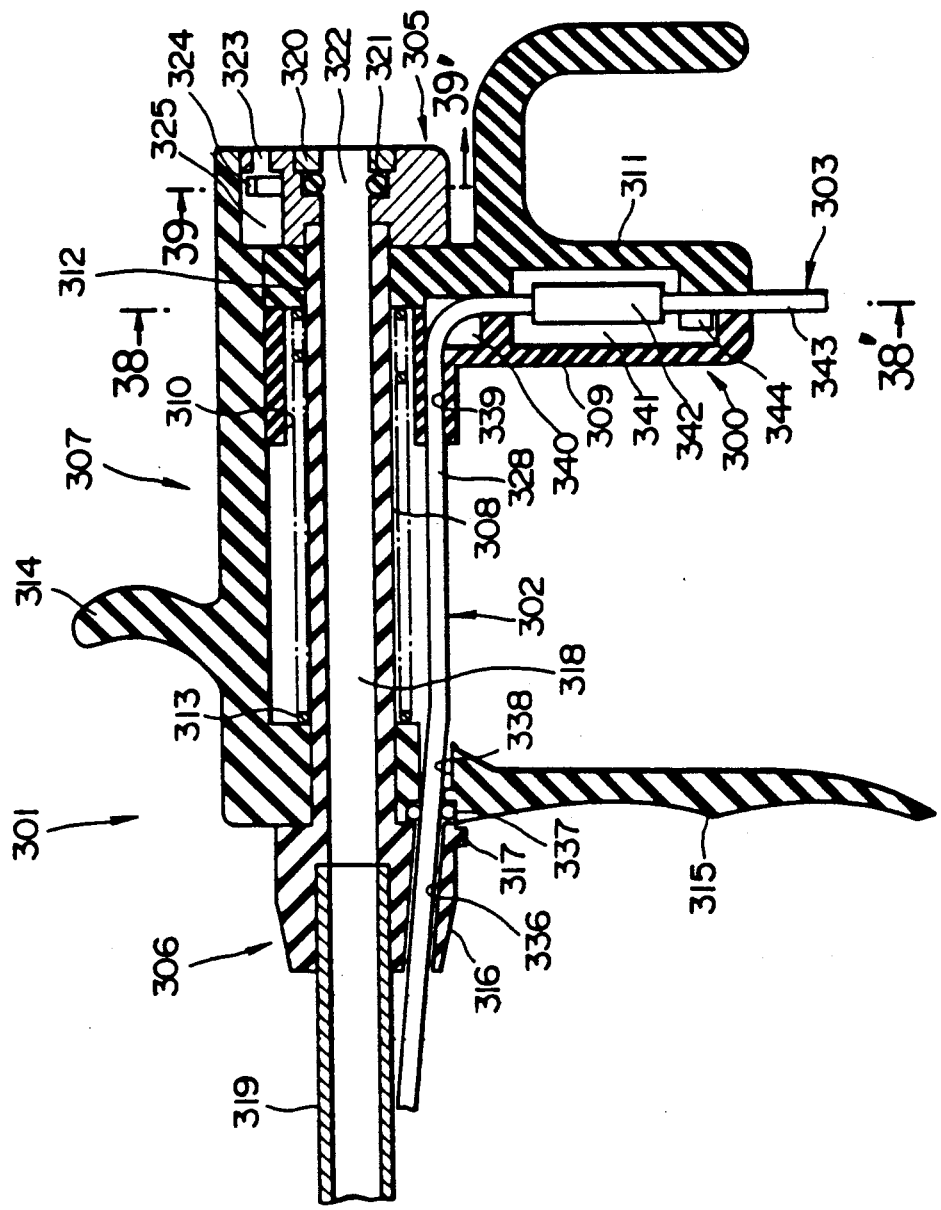
Figure 38:
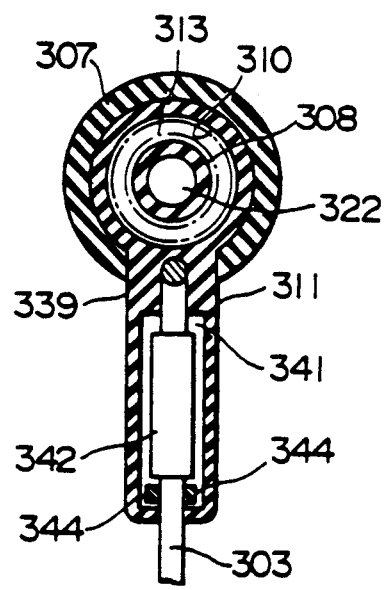
Figure 39:
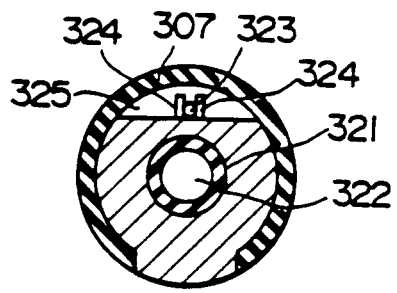
Figure 40:
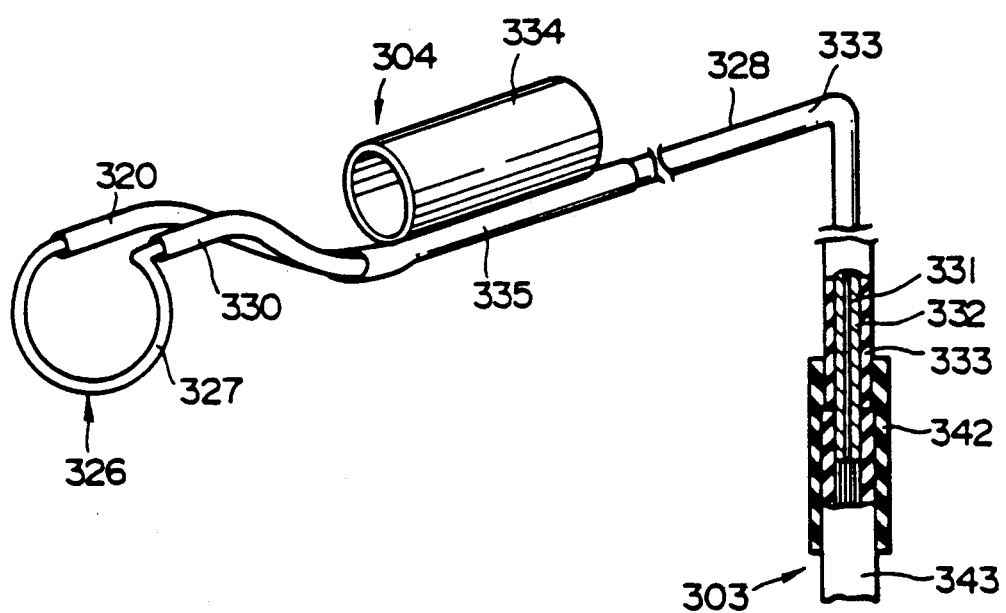

FIG. 29 shows the seventh embodiment of the present invention.

In this embodiment, the sheath connecting part 164, tapered part 165, pin 166, cover 169, lower finger hangar 171, upper finger hanger 172 and spring shaft 174 of the sixth embodiment are formed of such electric insulating material as plastics. The body 6 which is a connecting part on the sheath side is formed also of such electric insulating material as plastics.

The other formations and operations are the same as in the sixth embodiment.

In this embodiment, as the body 6 which is a connection part of the sheath 2 is formed of such electric insulating material as plastics, the current leaking to the patient and operator through the body 6 of the sheath 2 can be positively prevented from flowing.

The other effects are the same as in the sixth embodiment.

FIGS. 30 to 35 show the eighth embodiment of the present invention.

In this embodiment, a guide tube is provided with an electrode inserting hole and is formed integrally with a body.

In an operating part of this embodiment, a sheath connecting part 164, cover 169, lower finger hanger 171 and upper finger hanger 172 are integtally molded together with a guide tube 252. This guide tube 252 is provided with an optical sighting tube inserting hole 255 in the lengthwise direction and, as shown in FIG. 33, parallel electrode inserting holes 256 are parallelly provided on both sides of the lower part of this optical sighting tube inserting hole 255. An electrode part 253 is inserted through the electrode inserting holes 256 and is led to a slider part 254 through the sheath connecting part 164. An electrode part 253 is bent downward within spaces 199 provided between a slider front part 259 and slider rear part 260. The end part on one side of the electrode part 253 leads to a groove 200 provided between the slider front part 259 and slider rear part 260 from the space 199. The end part on the other side of the electrode part 253 is exposed out of the slider part 254 through a groove 261 provided between the slider front part 259 and slider rear part 260 from the space 199. The end part of this exposed electrode part 253 is connected to a wire, 191 as in FIG. 35 as a plug 263 made of a metal that is conductive and can be removably connected with a connector 265 provided at one end of the cord part 264.

The other formations are the same as in the sixth embodiment.

According to this embodiment, as the sheath connecting part, cover, lower finger hanger, upper finger hanger and operating part are integrally molded, the assemblability of the resectoscope apparatus can be improved.

The other effects are the same as in the sixth embodiment.

FIGS. 36 to 40 show the ninth embodiment of the present invention.

In this embodiment, an operating part 301 comprises a sheath connecting part 306 removably connected with a sheath in the front, a body 307 connected to the rear of this sheath connecting part, an optical sighting tube connecting part 305 provided in the rear of this body 307, a slider part 300 provided slidably forward and rearward within the above mentioned body 307 and an electrode 304 formed integrally with an electrode part 302 and cord part 303, fixed to the above mentioned slider part 300 and movable forward and rearward.

The above mentioned bodY 307 is cylindrically formed of such electric insulating material as plastics and is opened on the lower peripheral wall surface and in the rear. An insulating pipe 308 formed of such electric insulating material as plastics and provided in the rear of the sheath connecting part 306 passes rearward from the front end surface of this body 307 and is internally fitted at the rear end to the front end surface of the above mentioned optical sighting tube connecting part 305 provided in the opened part in the rear of the body 307. An optical sighting tube hole 318 which, is a tube path of the insulating pipe 308 communicates with an optical sighting tube inserting hole 322 provided in the optical sighting tube connecting part 305.

The above mentioned slider part 300 consists of a slider front part 309 and slider rear part 311. In the upper part of the slider front part 309, a spring hole 310 passes from the front end surface to the rear end surface. Further, in the upper part of the slider rear part 311, a guide hole 312 communicating with the above mentioned spring hole 310 passes. The inside diameter of the guide hole 312 is somewhat larger than the outside diameter of the insulating pipe 308. The inside diameter of the spring hole 310 is larger than the diameter of the guide hole 312. A coil spring 313 is wound on the insulating pipe 308, contacts at the front end with the rear end surface of the body 307 and is inserted at the rear end through a spring hole 310 to contact the front end surface of the slider rear part 311. The insulating pipe 308 is inserted through the spring hole 310 and guide hole 312 to lead to the optical sighting tube connecting part 305. The coil spring 313 as energized is provided on the insulating pipe 308 to keep the slider part 300 butted against the optical sighting tube connecting part 305.

An upper finger hanger 314 on which the forefinger may be hung in case the operating part 301 is held with one hand and which is provided on the front upper surface of the above mentioned body 307 and a lower finger hanger 315 on which the middle finger and third finger may be hung and which is provided on the front lower surface are molded of such electric insulating material as plastics integrally with the body 307.

Such tapered part 316 as becomes smaller forward in the diameter is provided in the front part of the above mentioned sheath connecting part 306. In the rear of this tapered part 316, a pin 317 is provided to project in the diametral direction. The sheath 2 is externally fitted to this tapered part 316 and is engaged, with the pin 317 so as to be removably connected. The tapered part 316 and pin 317 are molded of such electric insulating material as plastics integrally with the sheath connecting part 306.

A guide tube 319 having the same inside diameter as of the optical sighting tube hole 318 which is a tube path within the insulating pipe 308 is internally fitted to the front end surface of the sheath connecting part 306 and communicates in the tube path with the optical sighting tube hole 318.

An 0-ring 321 is fixed by an 0-ring presser 320 on the inner peripheral surface of the optical sighting tube inserting hole 322 of the above mentioned optical sighting tube connecting part 305 and is provided to keep watertightness between the insertable part 95 and optical sighting tube inserting hole 322 in case the optical sighting tube 94 is inserted.

A pin hole 323 in which the connection pin 97 is inserted is provided above the optical sighting tube inserting hole 322 on the rear end surface of the above mentioned optical sighting tube connecting part 305 and communicates with a space 325 provided within the optical sighting tube connecting part 305. In front of the pin hole 323 within this space 325, clicks 324 project with a width slightly smaller than the outside diameter of the connecting pin 97 so as to engage the connecting pin 97 so that the optical sighting tube 94 may be removably connected.

The tip part of the above mentioned electrode part 302 is provided as a loop 327 formed so that a wire 326 may internally contact the inside wall of the sheath 2. The wire 326 rearward from both ends of the loop 327 is coated with stainless steel pipes 329 to improve the bending strength and is further electrically insulated and coated on the stainless steel pipes 329 with Teflon tubes 330. The wire 326 is extended rearward from both ends of the loop 327 and is bent downward along the outer periphery of the guide tube 317 near the tip part of the guide tube 319. The thus bent wire 326 parts are combined into one below the guide tube 319 and are connected to a shaft 328.

The above mentioned shaft 328 has a wire 331 inserted through a stainless steel pipe 332 which is electrically insulated and coated on the outer periphery with a Teflon tube 333. The wire 331 on this shaft 328 side and the wire 326 combined into one are pressed and fixed by the stainless steel pipe 332. This pressed part is coated with a Teflon tube 333 and is further coated on the Teflon tube 333 with a pipe 335 bonded with a tubular stabilizer 334. The guide tube 319 is slidably internally inserted in the stabilizer 334 so that the electrode part 302 may be stably movable forward and rearward.

The above mentioned shaft 328 is extended further rearward from the rear end of the pipe 335 and leads to the slider part 300 through an electrode hole 336 provided below the optical sighting tube hole 318 of the sheath connecting part 306 and a communicating hole 336 provided in the body 307 so as to communicate with this electrode hole 336. An 0-ring 337 is provided in the front end part of the communicating hole 338 to keep the watertightness on the sheath 2 side.

The electrode part 302 is inserted into an electrode hole 339 provided in the slider front part 309, is bent downward substantially at right angles within a space 340 communicating with this electrode hole 339 and is electrically connected with a cord 343 of a cord part 303 within a space 341 provided between the slider front part 309 and slider rear part 311. This connecting part is electrically insulated and coated with a thermocontracting tube 342. The cord 343 is held by a presser 344 having a width slightly smaller than the outside diameter of the cord 343 and provided within the space 341 of the slider rear part 311 so as not to be pulled out of the slider rear part 311. The cord 343 is extended out of the slider part 300 and is connected at the end with a plug 345 connectable to a high frequency current source not illustrated.

In this embodiment, as the reinforcing part is formed of a cylinder, the strength can be further elevated.

The other effects are the same as in the sixth embodiment.

As explained above, according to the present invention, a leaking current can be prevented from flowing to the patient and operator through the sheath connecting part or the guide tube so that the danger of a burn or electric shock may be eliminated and the electric safety may be elevated.

What is claimed is:

1. A resectoscope apparatus comprising:
   an elongate hollow sheath to be inserted into a body cavity;
   an electrode inserted through said sheath and resecting or coagulating tissues within the body cavity by using a high frequency current;
   an endoscope insertable part inserted through said sheath and having an optical system with which the body cavity interior can be observed; and
   an operating part having a guide tube part through which said endoscope insertable part is inserted and a sheath connecting part connected to the base end part of said sheath and making said electrode operatable from outside the body, at least one of said guide tube part and sheath connecting part being formed of an electric insulating material for electric insulation.

2. A resectscope apparatus according to claim 1 wherein said operating part comprises a guide tube through which said endoscope insertable part is inserted, a sheath connecting member through which said guide tube is inserted and a slider part connected with said electrode and sliding on said guide tube said guide tube being formed of an electric insulating material.

3. A resectoscope apparatus according to claim 1 wherein said operating part comprises a guide tube through which said endoscope insertable part is inserted, a sheath connecting member through which said guide tube is inserted and which is formed of an electric insulating material and a slider member connected with said electrode and sliding on said guide tube.

4. A resectoscope apparatus according to claim 1 wherein said operating part comprises a sheath connecting member connecting said sheath and formed of an electric insulating material, a metal guide tube inserted through said sheath connecting member, said guide tube internally receiving said endoscope insertable part and being coated with an insulating pipe, and a slider member slidable on said insulating pipe of said guide tube, said slide member being connected with said electrode and formed of an electric insulating material.

5. A resectoscope apparatus according to claim 1 wherein said operating part comprises a sheath connecting member connecting said sheath and formed of an electric insulating material, a first guide tube which is provided in the front end part of said sheath connecting part and through which said endoscope insertable part is inserted, a slider member connected with said electrode and formed of an electric insulating material and a second guide tube on which said slider member slides, which communicates with said first guide tube, through which said endoscope insertable part is inserted and which is formed of an electric insulating material.

6. A resectoscope apparatus according to claim 1 wherein said operating part comprises a guide tube through which said endoscope insertable part is inserted and which is formed of an electric insulating material, a sheath connecting part through which said guide tube is inserted and which is formed of an electric insulating material and a slider member connected with said electrode, sliding on said guide tube and formed of an electric insulating material.

7. A resectoscope apparatus according to claim 1 wherein said operating part is formed of an electric insulating material integrally with said guide tube part and sheath connection part.

8. A resectoscope apparatus according to claim 5 wherein said second guide tube is fitted to said sheath connecting member.

* * * * *